(12) United States Patent
Mitri

(10) Patent No.: US 10,676,706 B1
(45) Date of Patent: Jun. 9, 2020

(54) METHOD OF ORGANIZING AND VIEWING PROCESS DATA FROM DISPARATE EQUIPMENT

(71) Applicant: ONE HILL SOLUTIONS, LLC, Hopedale, MA (US)

(72) Inventor: Rami Mitri, Hopedale, MA (US)

(73) Assignee: ONE HILL SOLUTIONS, LLC, Hopedale, MA (US)

( * ) Notice: Subject to any disclaimer, the term of this patent is extended or adjusted under 35 U.S.C. 154(b) by 478 days.

(21) Appl. No.: 15/444,012

(22) Filed: Feb. 27, 2017

(51) Int. Cl.
*G05B 15/02* (2006.01)
*C12M 1/36* (2006.01)
*C12Q 3/00* (2006.01)

(52) U.S. Cl.
CPC ............... *C12M 41/48* (2013.01); *C12Q 3/00* (2013.01); *G05B 15/02* (2013.01)

(58) Field of Classification Search
CPC ........................... G06Q 10/10; G06F 19/3418
See application file for complete search history.

(56) References Cited

U.S. PATENT DOCUMENTS

| 7,398,187 | B2 | 7/2008 | Tinseth | ........................ | 702/187 |
| 2005/0158701 | A1* | 7/2005 | West | ..................... | C12M 41/48 435/3 |
| 2005/0176140 | A1* | 8/2005 | Benedict | ................ | C12M 23/58 435/366 |
| 2013/0245830 | A1* | 9/2013 | West | ..................... | C12M 41/48 700/266 |

* cited by examiner

*Primary Examiner* — Shogo Sasaki
(74) *Attorney, Agent, or Firm* — Sunstein LLP

(57) ABSTRACT

A bioprocess management system includes a bioprocess management controller for electronically interfacing with at least one bioreactor and at least one analyzer. Each bioreactor is configured to maintain cells based on a set of bioreactor operating parameters and to output bioreactor data. Each analyzer is configured to analyze at least one sample taken from at least one bioreactor and to output analyzer data for each sample. The bioprocess controller is configured to receive bioreactor data and analyzer data in real-time. Furthermore, the bioprocess controller is configured to correlate, in real-time, analyzer data from at least one analyzer with bioreactor data from at least one corresponding bioreactor. Additionally, the bioprocess controller is configured to output real-time data relating to at least one bioreactor operating parameter. The real-time data is based at least in part on correlated data from at least one analyzer and at least one corresponding bioreactor.

20 Claims, 33 Drawing Sheets
(30 of 33 Drawing Sheet(s) Filed in Color)

| PARAMETER | MAX | MIN | AVERAGE | STD DEVIATION |
|---|---|---|---|---|
| CO2 % | 37.56 | 23.56 | 29.91 | 2.34 |
| Temperature c | 32.47 | 30.63 | 31.35 | 0.28 |
| DO % | 6.73 | 6.6 | 6.64 | 0.02 |
| RPM RPM | 125.2 | 120.31 | 125.8 | 1.78 |
| Media ml/hg | 31.82 | 27.01 | 29.5 | 1.02 |
| N2 % | 37.82 | 31.5 | 34.46 | 1.07 |
| pH | 8.1 | 4.9 | 6.43 | 0.54 |
| PCO2 % | 18.23 | 15.62 | 16.8 | 0.44 |

| PARAMETER | MAX | MIN | AVERAGE | STD DEVIATION |
|---|---|---|---|---|
| Cell Density cells/ves | 31.61 | 12.23 | 22.3 | 6.06 |
| pH | 31.61 | 8.25 | 18.66 | 6.31 |
| CO2 % | 32.04 | 8.25 | 19.78 | 6.48 |
| PCO2 % | 32.04 | 8.25 | 18.58 | 6.36 |

Fig. 13

Figure 16:
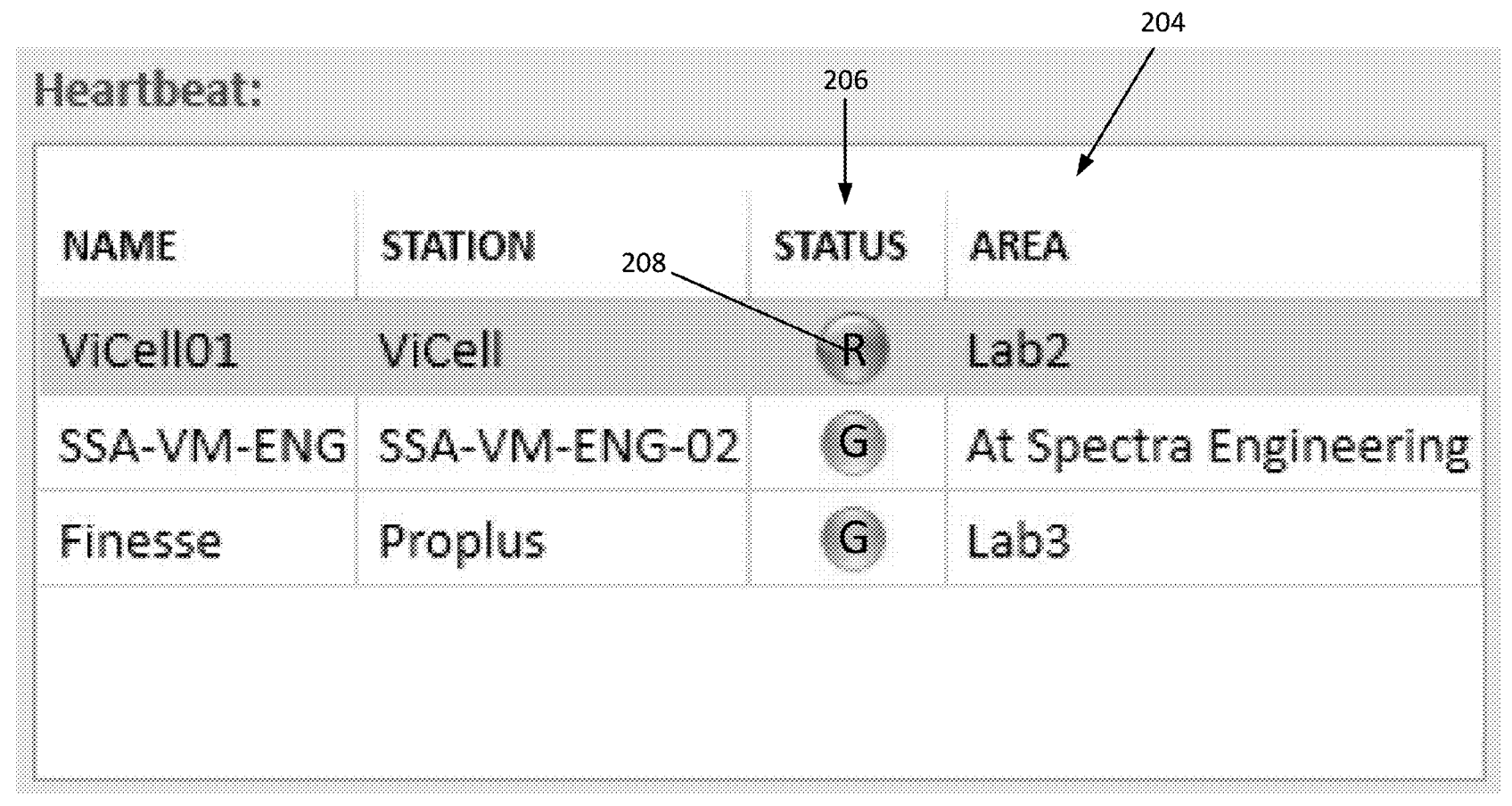

Heartbeat:

| NAME | STATION | STATUS | AREA |
|---|---|---|---|
| ViCell01 | ViCell | R | Lab2 |
| SSA-VM-ENG | SSA-VM-ENG-02 | G | At Spectra Engineering |
| Finesse | Proplus | G | Lab3 |

| Timestamp | Batch Id | Temperature c | DO % | N2 % | Vessel1Test |
|---|---|---|---|---|---|
| 06-Dec-2016 11:29 | 06-Dec-2001 | 31.53 | 6.63 | 34.61 | 7278.818139 |
| 06-Dec-2016 12:29 | 06-Dec-2001 | 31.61 | 6.64 | 34.77 | 7297.809208 |
| 06-Dec-2016 13:29 | 06-Dec-2001 | 31.48 | 6.64 | 34.05 | 7117.97616 |
| 06-Dec-2016 14:29 | 06-Dec-2001 | 31.6 | 6.62 | 31.6 | 6652.3056 |
| 06-Dec-2016 15:29 | 06-Dec-2001 | 31.37 | 6.65 | 34.57 | 7211.888983 |
| 06-Dec-2016 16:29 | 06-Dec-2001 | 30.98 | 6.64 | 33.89 | 6963.359936 |
| 06-Dec-2016 17:29 | 06-Dec-2001 | 31.73 | 6.66 | 35.63 | 7529.395734 |
| 06-Dec-2016 18:29 | 06-Dec-2001 | 32.19 | 6.61 | 34.61 | 7135.401799 |
| 06-Dec-2016 19:29 | 06-Dec-2001 | 31.61 | 6.65 | 33.67 | 7077.652853 |
| 06-Dec-2016 20:29 | 06-Dec-2001 | 31.42 | 6.64 | 35.1 | 7322.87018 |
| 06-Dec-2016 21:29 | 06-Dec-2001 | 31.11 | 6.64 | 35.62 | 7358.037648 |
| 06-Dec-2016 22:29 | 06-Dec-2001 | 31.36 | 6.61 | 34.6 | 7172.22016 |
| 06-Dec-2016 23:29 | 06-Dec-2001 | 31.39 | 6.62 | 34.62 | 7117.21165 |
| 07-Dec-2016 0:29 | 06-Dec-2001 | 31.07 | 6.63 | 34.34 | 7131.515742 |
| 07-Dec-2016 1:29 | 06-Dec-2001 | 31.01 | 6.64 | 34.89 | 7070.825776 |
| 07-Dec-2016 2:29 | 06-Dec-2001 | 31.8 | 6.64 | 33.88 | 7354.42418 |
| 07-Dec-2016 3:29 | 06-Dec-2001 | 31.21 | 6.65 | 33.43 | 7031.67542 |
| 07-Dec-2016 4:29 | 06-Dec-2001 | 31.19 | 6.64 | 33.28 | 6925.62624 |
| 07-Dec-2016 5:29 | 06-Dec-2001 | 31.3 | 6.62 | 35.92 | 6902.77123 |
| 07-Dec-2016 6:29 | 06-Dec-2001 | 31.32 | 6.63 | 34.16 | 7442.88951 |
| 07-Dec-2016 7:29 | 06-Dec-2001 | 33.3 | 6.67 | 34.92 | 7093.378656 |
| 07-Dec-2016 8:29 | 06-Dec-2001 | 31.73 | 6.62 | 33.28 | 6990.558528 |
| 07-Dec-2016 9:29 | 06-Dec-2001 | 31.42 | 6.68 | 33.39 | 7226.266668 |
| 07-Dec-2016 10:29 | 06-Dec-2001 | 31.75 | 6.64 | 34.04 | 7144.503624 |
| 07-Dec-2016 11:29 | 06-Dec-2001 | 32.47 | 6.68 | 33.24 | 7007.65568 |
| 08-Dec-2016 12:29 | 06-Dec-2001 | 31.08 | 6.73 | 37.62 | 7910.748868 |
| 08-Dec-2016 12:29 | 06-Dec-2001 | 31.66 | 6.64 | 34.59 | 7271.59281 |

Fig. 31

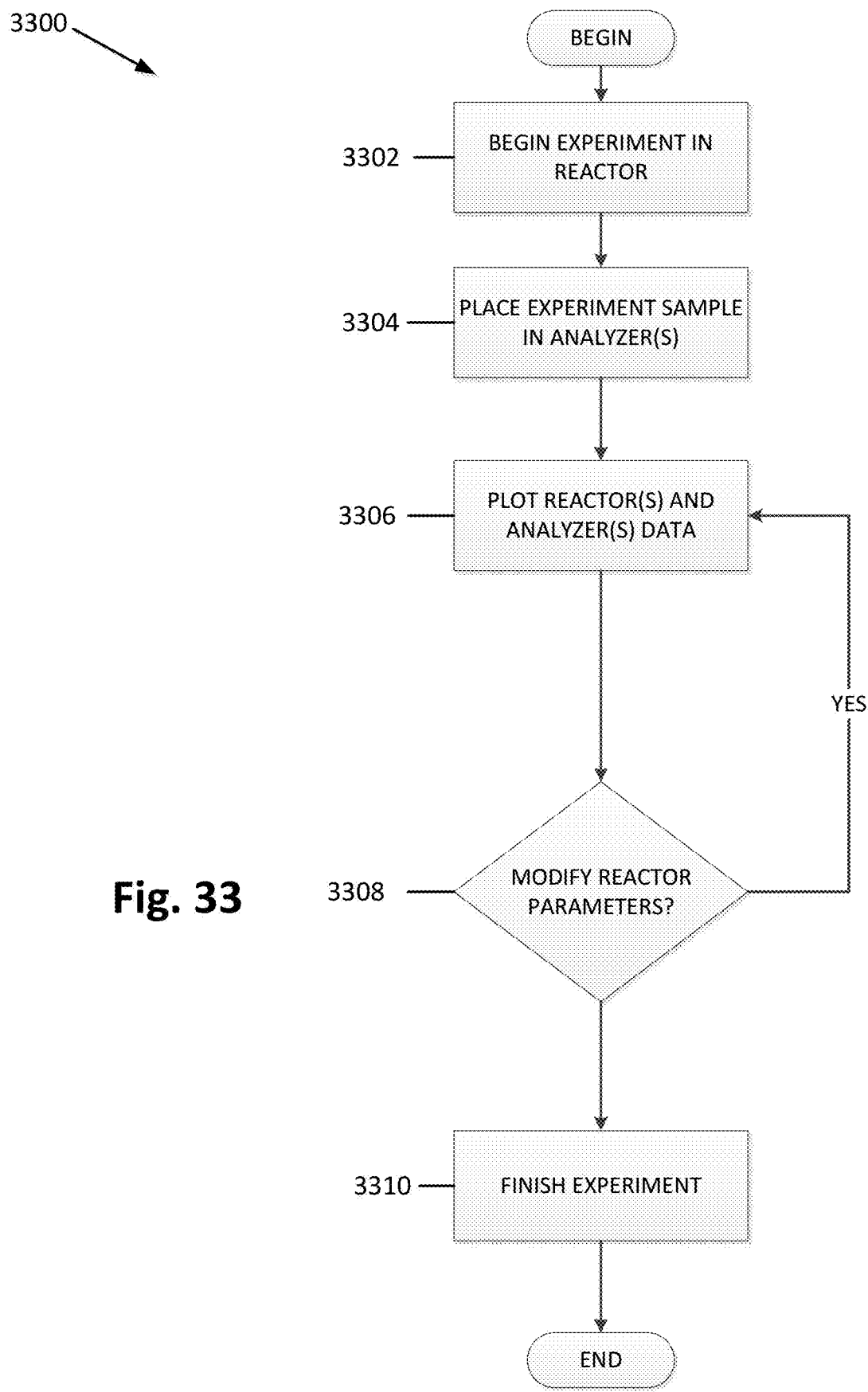

METHOD OF ORGANIZING AND VIEWING PROCESS DATA FROM DISPARATE EQUIPMENT

FIELD OF THE INVENTION

The invention generally relates to lab and/or manufacturing facilities having reactors and, more particularly, the invention relates to a system that allows disparate equipment to communicate in real time.

BACKGROUND OF THE INVENTION

Pharmaceutical and biotechnology companies use reactors, including bioreactors and chemical reactors, and analyzers to assist in the development of pharmaceuticals. A bioreactor is a device that supports a biologically active environment. The bioreactor may be used to run a process (e.g., an experiment growing cell cultures or a molecular production process), and may output a number of parameters relating to the cell culture. Analyzers also output data relating to cell culture parameters. A sample may be drawn from the bioreactor and placed in the analyzer for further analysis.

SUMMARY OF VARIOUS EMBODIMENTS

In accordance with one embodiment of the invention, a bioprocess management system includes a bioprocess management controller for electronically interfacing with at least one bioreactor and at least one analyzer. Each bioreactor is configured to maintain a population of cells based on a set of bioreactor operating parameters and to output bioreactor data. Each analyzer is configured to analyze at least one sample taken from at least one bioreactor. Each analyzer is further configured to output analyzer data for each sample. The bioprocess management controller is configured to receive bioreactor data and analyzer data in real-time. Furthermore, the bioprocess management controller is configured to correlate, in real-time, analyzer data from at least one analyzer with bioreactor data from at least one corresponding bioreactor. Additionally, the bioprocess management controller is configured to output real-time data relating to at least one bioreactor operating parameter. The real-time data may be based at least in part on the correlated data from the at least one analyzer and the at least one corresponding bioreactor.

The real-time data is based at least in part on correlated data from the at least one analyzer and the at least one corresponding bioreactor. To that end, the bioprocess management controller may include a driver for each bioreactor and a driver for each analyzer. Thus, the bioprocess management controller may receive the bioreactor data and analyzer data using the drivers. In some embodiments, the analyzer data may be discrete data.

The bioprocess management controller may be configured to repeatedly adjust at least one bioreactor operating parameter based at least in part on the real-time data. The bioprocess management controller may be configured to perform a calculation on the real-time data according to a formula, and the calculation may be used to adjust the at least one bioreactor operating parameter. Among other ways, the bioprocess management controller may be configured to automatically adjust the at least one bioreactor operating parameter based on comparisons between the real-time data and batch data in memory. For example, the batch data in memory may be golden batch data.

Furthermore, the bioprocess management controller may be configured to output real-time data as graphical indicia. Thus, the bioprocess management controller may be configured to synchronize the bioreactor data and the analyzer data and to display the synchronized data simultaneously in real-time.

Additionally, the system may include the at least one bioreactor and the at least one analyzer. At least one of the bioreactor operating parameters may be imported from a template. The sample may include a population of cells. The bioprocess management controller may be configured to adjust at least one bioreactor operating parameter to mitigate or prevent death of the cells.

In accordance with another embodiment of the invention, a method of managing reactor operating parameters includes electronically interfacing a process management controller with at least one reactor and at least one analyzer. The at least one reactor is configured to maintain a process based on a set of reactor operating parameters and to output reactor data. The at least one analyzer is configured to analyze at least one sample from the process, and each sample taken from the at least one reactor. Each analyzer is further configured to output analyzer data for each sample. The method also receives the reactor data and analyzer data in real-time. The method correlates, in real-time, the analyzer data from the at least one analyzer with the reactor data from the at least one corresponding reactor. The method also outputs real-time data relating to the at least one reactor operating parameter relative to the process.

In accordance with another embodiment of the invention, a process management system includes a process management controller for electronically interfacing with at least one chemical reactor and at least one analyzer. The at least one chemical reactor is configured to contain a chemical reaction based on a set of reactor operating parameters. The chemical reactor is also configured to output chemical reactor data. The at least one analyzer is configured to analyze at least one sample from the chemical reaction, and each sample taken from the at least one chemical reactor. Each analyzer is further configured to output analyzer data for each sample. The process management controller is configured to receive the chemical reactor data and the analyzer data in real-time. The process management controller also correlates, in real-time, the analyzer data from the at least one analyzer with the reactor data from at least one corresponding chemical reactor. The process management controller may also output real-time data relating to at least one reactor operating parameter relative to the chemical reaction.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized below. The patent or application file contains at least one drawing executed in color. Copies of this patent with color drawing(s) will be provided by the Patent and Trademark Office upon request and payment of the necessary fee.

FIG. 7 shows bioreactor data for a single batch that has been averaged over a timespan, in accordance with illustrative embodiments of the invention.

FIG. 8 shows analyzer data associated with the single batch in FIG. 7.

FIG. 9 shows a summary page of selected vessel data and corresponding analyzer data, in accordance with illustrative embodiments of the invention.

FIG. 13 shows a report generated under the report tab, in accordance with illustrative embodiments of the invention.

FIG. 16 shows a status identifier screen for the bioreactors and the analyzers connected to the bioprocess management unit, in accordance with illustrative embodiments of the invention.

FIG. 18 shows an interface for selecting active batches available for plotting, in accordance with illustrative embodiments of the invention.

FIG. 20 shows a screenshot of the live vessel data displayed in a table format, in accordance with illustrative embodiments of the invention.

FIG. 21 shows a screenshot of the live analyzer data displayed in a table format, in accordance with illustrative embodiments of the invention.

FIG. 29 shows an interface for using a formula to perform calculations on the collected data, in accordance with illustrative embodiments.

FIG. 31 shows a formula spreadsheet created by a formula, in accordance with illustrative embodiments of the invention.

FIG. 33 is a flowchart schematically illustrating an experiment, in accordance with one exemplary embodiment of the invention.

DESCRIPTION OF ILLUSTRATIVE EMBODIMENTS

In illustrative embodiments, a process management unit integrates communication between various brands (referred to as "disparate" devices) of reactors and various brands of analyzers. The process management unit is operatively linked to all of the reactors and analyzers. Interface drivers are developed for each different brand of device, allowing for real-time data collection and utilization among the disparate devices. The real-time data can be used to adjust reactor operating parameters (e.g., temperature) on the fly. Details of illustrative embodiments are discussed below.

Figure 1:
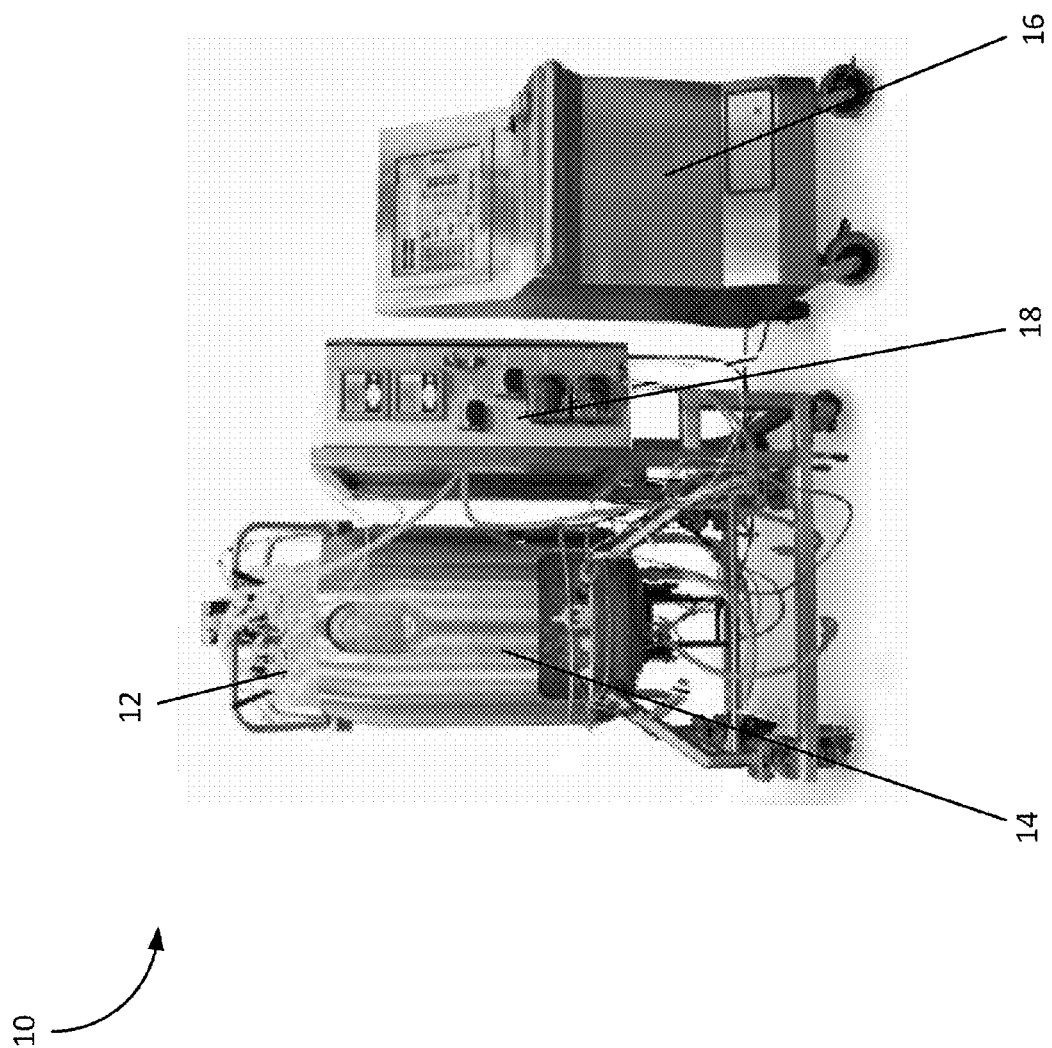
FIG. 1 schematically shows a bioreactor, in accordance with illustrative embodiments of the invention.

FIG. 1 schematically shows a reactor 10. The reactor may be, for example, a bioreactor or a chemical reactor. As shown in FIG. 1, the reactor 10 is a bioreactor 10. Bioreactors 10 are used for cell cultivation. The bioreactor 10 includes a stainless steel vessel 14, which may contain a disposable bag 12. Cells and growth media are added to the disposable bag 12, and the growth environment in the bag 12 is monitored and controlled by the bioreactor 10 using, for example, a control system 16. The control system 16 controls bioreactor operating parameters, which are the parameters of the growth environment of the cell culture within the vessel 14. The bioreactor operating parameters may include, for example, pH, dissolved oxygen concentration, weight and media distribution, carbon dioxide concentration, oxygen concentration, gas flow rate, and/or temperature. Bioreactor operating parameters may also be referred to as vessel operating parameters.

The bioreactor 10 may also include an input-output cabinet 18 (also referred to as an "TO cabinet 18"). The TO cabinet 18 physically and logically connects the vessel 14 with the controller 16. The TO cabinet 18 contains instrumentation for the measurement and control of all of the bioreactor operating parameters. The TO cabinet 18 may include, among other things, pumps, bag pressure transmitters, pH sensors/transmitters, DO sensors/transmitters, and/or temperature sensors/transmitters. Thus, the bioreactor operating parameters may be measured and/or modified by sending instructions from the control system 16 to the TO cabinet 18. It is common to measure and record bioreactor operating parameters, for example, every 5 seconds (i.e., the sampling rate) throughout the entire course of a reactor process (e.g., an experiment or a production process). However, the sampling rate may be variable and user selectable.

The TO cabinet 18 may be coupled to various actuators and/or controllers that modify the reactor operating parameters. For example, the TO cabinet 18 may be coupled with a pH controller (not shown) that controls the pH of the growth environment. The pH controller may include an actuator and/or electronics that may be coupled to a CO2 pump and/or an acid pump and a base pump. The actuator pumps CO2, acid, and/or base into the growth environment to modify the pH in accordance with instructions received from the control system 16. In some embodiments, the IO cabinet 18 may include the various actuators and/or controllers.

It should be understood that the various parts of the bioreactor system 10 have been simplified. The bioreactor system 10 may contain a number of components not listed herein, and/or may combine or separate the aforementioned components (e.g., IO cabinet 18 and control system 16). Furthermore, the bioreactor 10 shown is not intended to limit illustrative embodiments of the invention. A number of different vendors (e.g., General Electric, Thermo Systems, Finesse Solutions, Sartorius, Applikon, etc.) produce different types of bioreactors 10 (e.g., stirred-tank, wave-rocker) that are compatible with illustrative embodiments of the invention.

Figure 2:
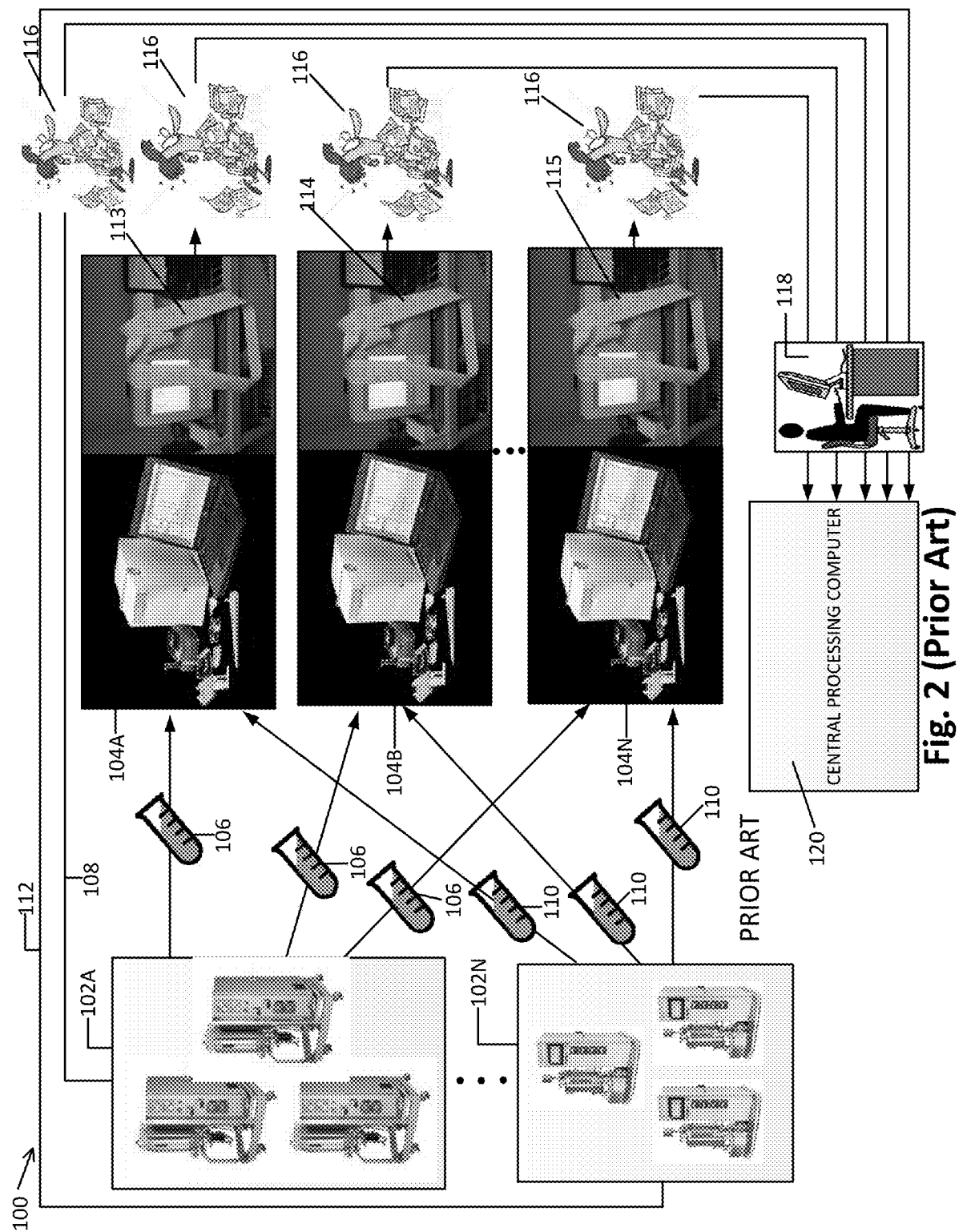
FIG. 2 schematically shows a lab environment of the prior art with groupings of bioreactors and analyzers, in accordance with illustrative embodiments of the invention.

FIG. 2 schematically shows a lab environment 100 of the prior art with groupings of bioreactors 102A, . . . 102N and analyzers 104A, 104B, . . . 104N. Although illustrative embodiments describe a lab environment 100, this is not intended to limit illustrative embodiments of the invention. In some embodiments, for example, the environment 100 may be in a manufacturing facility. Additionally, although illustrative embodiments describe experiments, it should be understood that in some embodiments the process may be a manufacturing process.

Each different grouping of bioreactors 102A-102N and grouping of analyzers 104A-104N may include a plurality of the same devices (e.g., the same model bioreactor 10). As shown, a first grouping of bioreactors 102A grows cell cultures and outputs bioreactor data 108 that is related to that cell culture. Additionally, another grouping of bioreactors 102N is growing another cell culture, and outputting bioreactor data 112 that is related to its cell culture. Each individual bioreactor 10 in a grouping (e.g., 102A) grows an individual batch, which is associated with a batch identification number (also referred to as a "batch ID"). Although the bioreactors 102A-102N grow different batches, it should be understood that the cell cultures may, although are not required to, be the same.

Samples 106 and 110 are drawn from the disposable bag (or other sampling port) of each bioreactor and are placed within analyzer(s) 104A-104N to test for various parameters. Although the figure shows a single analyzer in each grouping 104A-104N, this is merely for illustrative convenience. Each analyzer 104A-104N may comprise a plurality of analyzers 104A-104N (e.g., the same model analyzer).

The analyzers 104A-104N output analyzer data 113-115 relating to the tested samples 106 and/or 110. Generally, the analyzers 104A-104N provide data 113-115 about parameters not generally measured in conventional reactors (e.g., bioreactors 102A-102N). Furthermore, different analyzers 104A-104N may output information relating to different types of parameters. Thus, lab environments 100 may have a variety of analyzers 104A-104N that are each able to output data 113-115 relating to the same and/or different sample 106 and 110 parameters. Although different reference numerals are used to distinguish biological samples 106 and 110, it should be understood that the reference numerals are intended to denote different bioreactor 102A-102N sources and that the samples 106 and 110 may be of the same type.

The analyzers 104A-104N measure and/or analyze the biological sample 106 or 110 and output analyzer data. The analyzer data may also be referred to as discrete transactional reports. These discrete transactional reports may include, for example, cell density, cell viability, aggregation rate, cell diameter and cell compactness. Additionally, or alternatively, the analyzers 104A-104N may provide information about metabolites, such as, among other things, the concentration of acetate, ammonia, calcium, cholesterol, formate, galactose, glucose, glutamate, glutamine, glycerol, IgG, iron, lactate, LDH, magnesium, optical density, phosphate, potassium, pyruvate, sodium, sucrose and/or total proteins.

Lab environments 100 often use a variety of disparate bioreactors 102A-102N and/or disparate analyzers 104A-104N obtained from different vendors. However, these disparate bioreactors 102A-102N are not able to communicate with each other, nor are they able to communicate with the analyzers 104A-104N. Instead, lab technicians 116 take the data 108, 112 and 113-115 and manually enter 118 it into a central processing computer 120 to organize and review the data 108, 112 and 113-115 in a central location. This presents a problem, however, because large amounts of data 108, 112, and 113-115 are produced. Thus, the centralization and organization of data 108, 112, and 113-115 from disparate lab equipment 102A-102N and 104A-104N is time consuming and prevents the real-time collection and modification of operating parameters.

Although the below examples refer to bioreactors 102A-102N, it should be understood that in illustrative embodiments the bioreactors 102A-102N may be interchangeable with chemical reactors. Accordingly, in illustrative embodiments discussion of bioreactor data also pertains to chemical reactor data.

Figure 3:
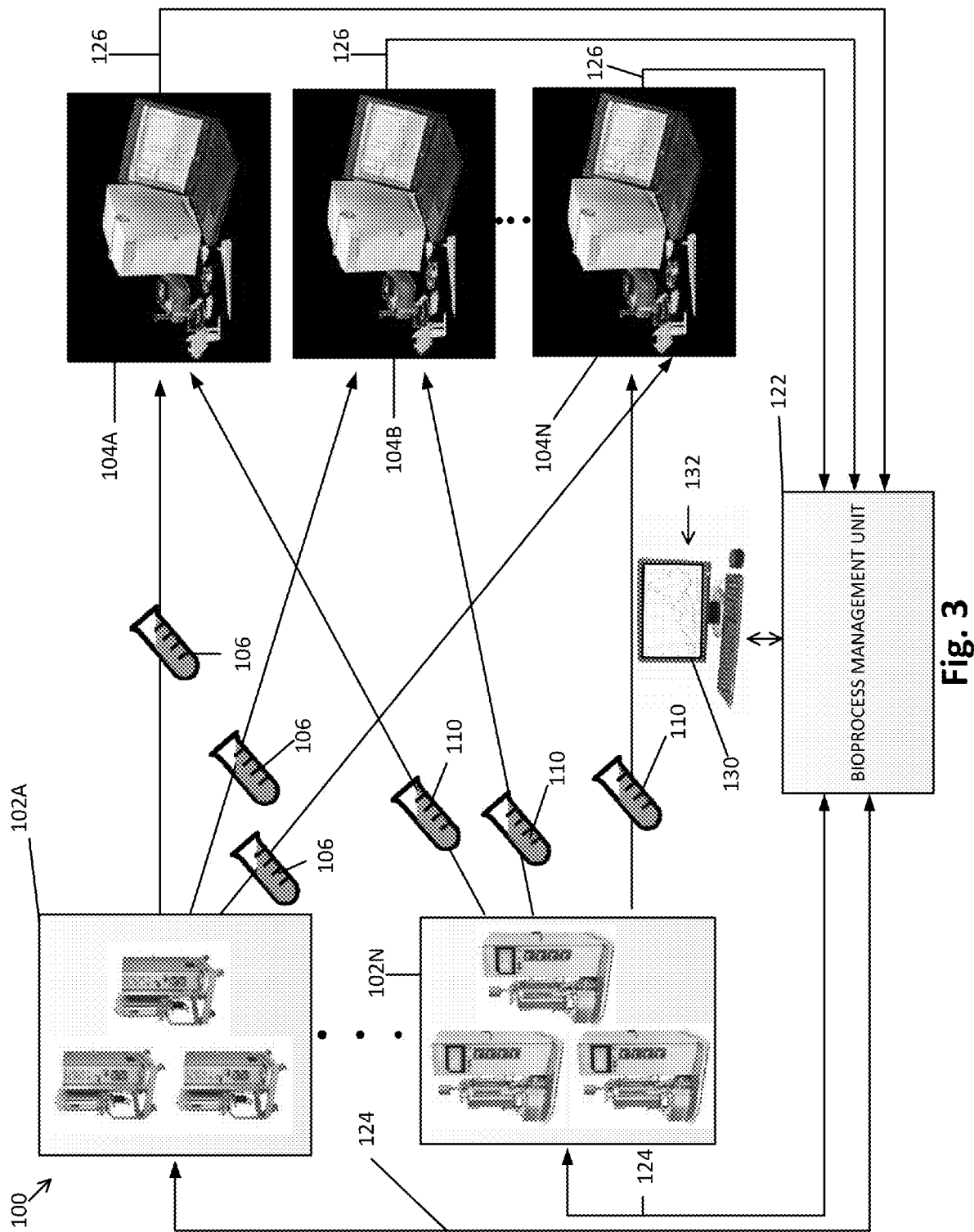
FIG. 3 schematically shows a lab environment where bioreactor data and analyzer data are processed, in accordance with illustrative embodiments of the invention.

FIG. 3 schematically shows a lab environment 100 where bioreactor data 124 and analyzer data 126 are processed in accordance with illustrative embodiments of the invention. The lab environment 100 shown in FIG. 3 is similar to that of FIG. 2, except a bioprocess management unit 122 couples directly with the disparate bioreactors 102A-102N and disparate analyzers 104A-104N. Each group of bioreactors 102A, 102B, . . . 102N may be from different vendors and/or different models from every other group of bioreactors 102A, 102B, . . . 102N. Similarly, each group of analyzers 104A, 104B, . . . 104N may be from different vendors and/or different from every other group of analyzers 104A, 104B, . . . 104N.

As described above, the bioreactors 102A-102N may have respective samples 106 and 110 that are placed into the analyzers 104A-104N. The analyzers 104A-104N output analyzer data 126 that is related to the sample 106 and/or 110. Generally, an analyzer 104A-104N analyzes a single sample 106 or 110 at a time. Although a single analyzer 104A-104N is shown, it should be understood that a plurality of each type of analyzers 104A, 104B and 104N may be used simultaneously.

Although FIG. 3 describes the bioreactor data 124 with a single reference numeral, the bioreactor data 108 and 112 in FIG. 2 is assigned different reference numerals. This is because, for example, the data type, the data format, and/or the parameters output may vary between the disparate bioreactors 102A and 102N. However, in illustrative embodiments the bioprocess management unit 122 has drivers configured to communicate (e.g., facilitate the input and output of data) between each different brand of device. Thus, all connected bioreactors 102A-102N are treated as having a uniform data 124 output when connected to the bioprocess management unit 122.

In a similar manner, the analyzer data 113-115 from FIG. 2 is also assigned different reference numerals. The bioprocess management unit 122 of FIG. 3 has drivers configured to communicate (e.g., facilitate the input and output of data) between each different brand of device. Thus, all connected analyzers 104A-104N are treated as having a uniform data 126 output when connected to the bioprocess management unit 122. Furthermore, although the connections to the bioprocess management unit 122 are shown as wired, some embodiments may operate over a wireless connection.

The bioreactors 102A-102N and the analyzers 104A-104N communicate directly with the bioprocess management unit 122, eliminating labor and time-intensive manual entry performed by technicians. Thus, data 124 from the bioreactors 102A-102N and data 126 from the analyzers 104A-104N may be input to the bioprocess management unit 122 in real-time. Accordingly, the bioprocess management unit 122 outputs real-time data 124 and/or 126 obtained from all of the connected analyzers 104A-104N and all of the connected bioreactors 102A-102N (e.g., as graphical indicia 130 on a user computer terminal 132). Because the data 124 connection is bi-directional (i.e., data can be input and output from the bioreactors 102A-102N to the bioprocess management unit 122), an input from any connected device in the lab 100 (e.g., user computer terminal 132, analyzer 104A-104N, and/or bioreactor 102A-102N) may be used to modify the operating parameters of the bioreactors 102A-102N in real-time (e.g., by communicating with the control system and/or communicating directly with the TO cabinet).

Figure 4:
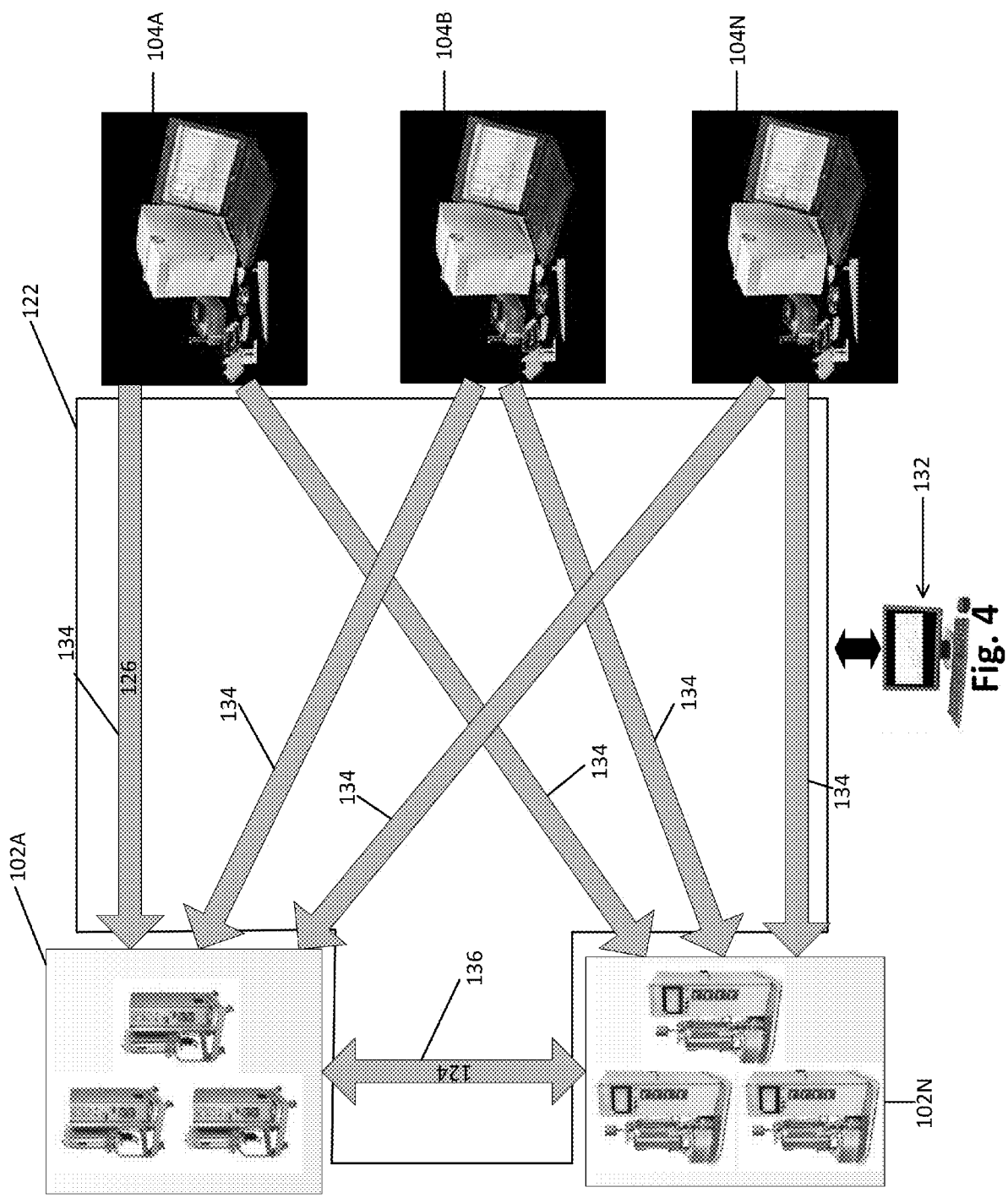
FIG. 4 schematically shows communication channels enabled by the bioprocess management unit of FIG. 3, in accordance with illustrative embodiments of the invention.

FIG. 4 schematically shows communication channels 134 enabled by the bioprocess management unit 122 of FIG. 3, in accordance with illustrative embodiments of the invention. The bioprocess management unit 122 establishes communication channels 134 between the analyzers 104A-104N and the bioreactors 102A-102N that were previously unavailable. Each of the analyzers 104A-104N may unilaterally output real-time data 126 to each of the bioreactors 102A-102N. The real-time data 126 may be a discrete analyzer transactional report, which contains parameter data relating to the sample from the bioreactor 102A-102N. For example, the analyzer 104A may output pH and/or glucose concentration to the bioprocess management unit 122, which may be used to modify at least one of the bioreactor operating parameters (e.g., temperature).

The bioprocess management unit 122 may automatically adjust the bioreactor operating parameters in real-time based on the real-time data 126 output by at least one of the analyzers in 104A-104N. Additionally, or alternatively, a technician at the user terminal 132 may adjust the bioreactor operating parameters based on the real-time data 126 output by at least one of the analyzers 104A-104N. In some embodiments, the bioreactor 102A operating parameters are adjusted based on the real-time data 126 output by a plurality of analyzers 104A, 104B, and/or 104N.

A communication channel 136 is also established between disparate types of bioreactors 102A and 102N. Real-time data 124 may be communicated (e.g., compared) between the various bioreactors 102A-102N. For example, bioreactor 102A may run an experiment at a pH of 7.5, while bioreactor 102N may run the same experiment at a pH of 8.0. If the bioprocess management unit 122 determines that a certain bioreactor operating parameter (i.e., pH in this example) is favorable, then the other bioreactor may be configured to automatically adjust its operating parameter to match. Thus, the bioprocess management unit 122 may automatically adjust the bioreactor operating parameters in real-time based on the real-time data 124 output by other bioreactors and/or analyzers (e.g., by sending a control signal to the pH actuator to pump CO2, acid and/or base into the growth environment).

In some embodiments, the bioreactor operating parameter may automatically be adjusted on the basis of data 124 and/or 126 from a plurality of channels 134 and 136. All of the foregoing communication channels may be real-time communication channels.

FIGS. 5-24 show screenshots of how data is recorded, displayed, and retrieved in accordance with illustrative embodiments of the invention.

Figure 5:
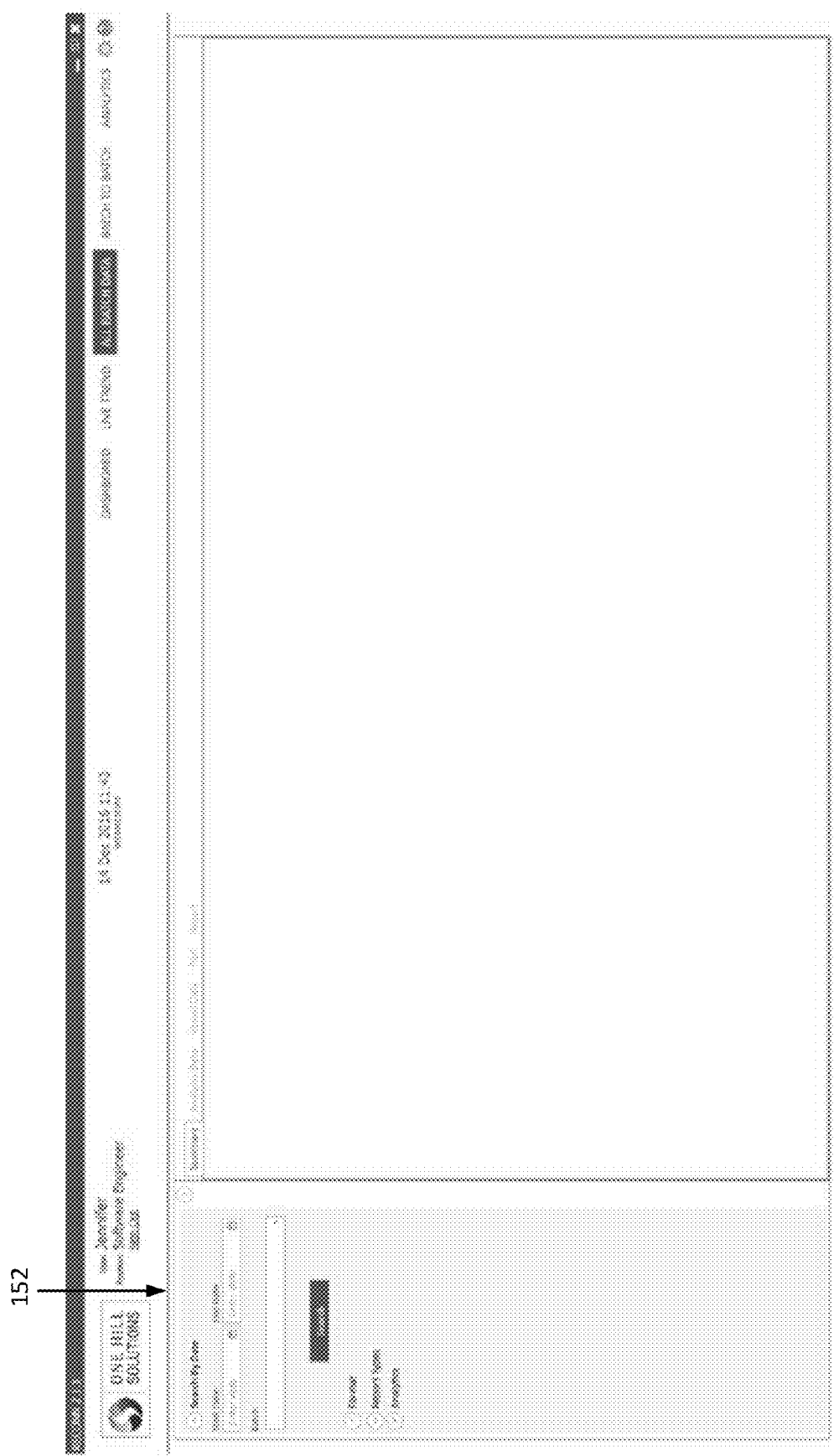
FIG. 5 shows a home screen where a user may view and/or search for batch data from a historian, in accordance with illustrative embodiments of the invention.

FIG. 5 shows a home screen where a user may view and/or search for batch data from a historian (i.e., record keeping database), in accordance with illustrative embodiments of the invention. As described above, each batch is related to a specific bioreactor culture. The same cells grown in four different bioreactors would result in four different batch IDs. The user interface has a search tab 152 that allows the user to search for specific batches.

Figure 6:
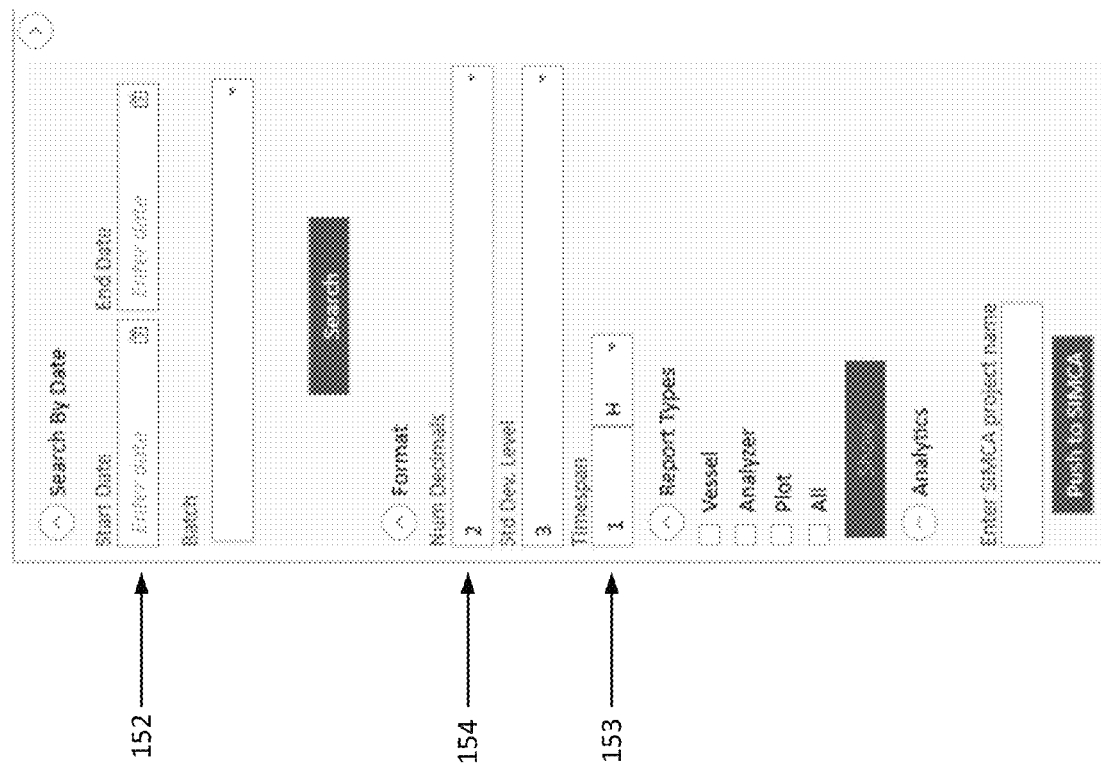
FIG. 6 shows the search tab and format tab of FIG. 5.

FIG. 6 shows the search tab 152 and a format tab 154. Users may search by a batch start date (i.e., when the bioreactor started measuring results). Additionally, or alternatively, the user may enter the batch ID if it is known. After entering search criteria, the user may select the data display format. For example, the number of decimal points (e.g., precision) in the data results may be selected. Additionally, the data timespan may be selected. The bioreactors each collect large amounts of data. For example, the bioreactor may collect data every five seconds over the course of a fourteen-day experiment.

In some embodiments, data is displayed in accordance with the selected timespan 153 interval. As shown, the timespan 153 is one-hour. The bioprocess management unit collects and averages data over the course of the timespan 153 (e.g., one-hour), and displays a single data point every hour. Thus, for three hours of data collection, three data points would be shown when the selected timespan 153 is 1-hour. For example, the first data point is an average of the data sampled from the beginning of the experiment until the first hour, the second data point is an average of the data sampled from after the first hour until the end of the second hour, and the third data point is an average of the data sampled from after the second hour until the end of the third hour. Timespans 153, however, may be relative to days, hours, minutes and/or seconds.

Figure 7:
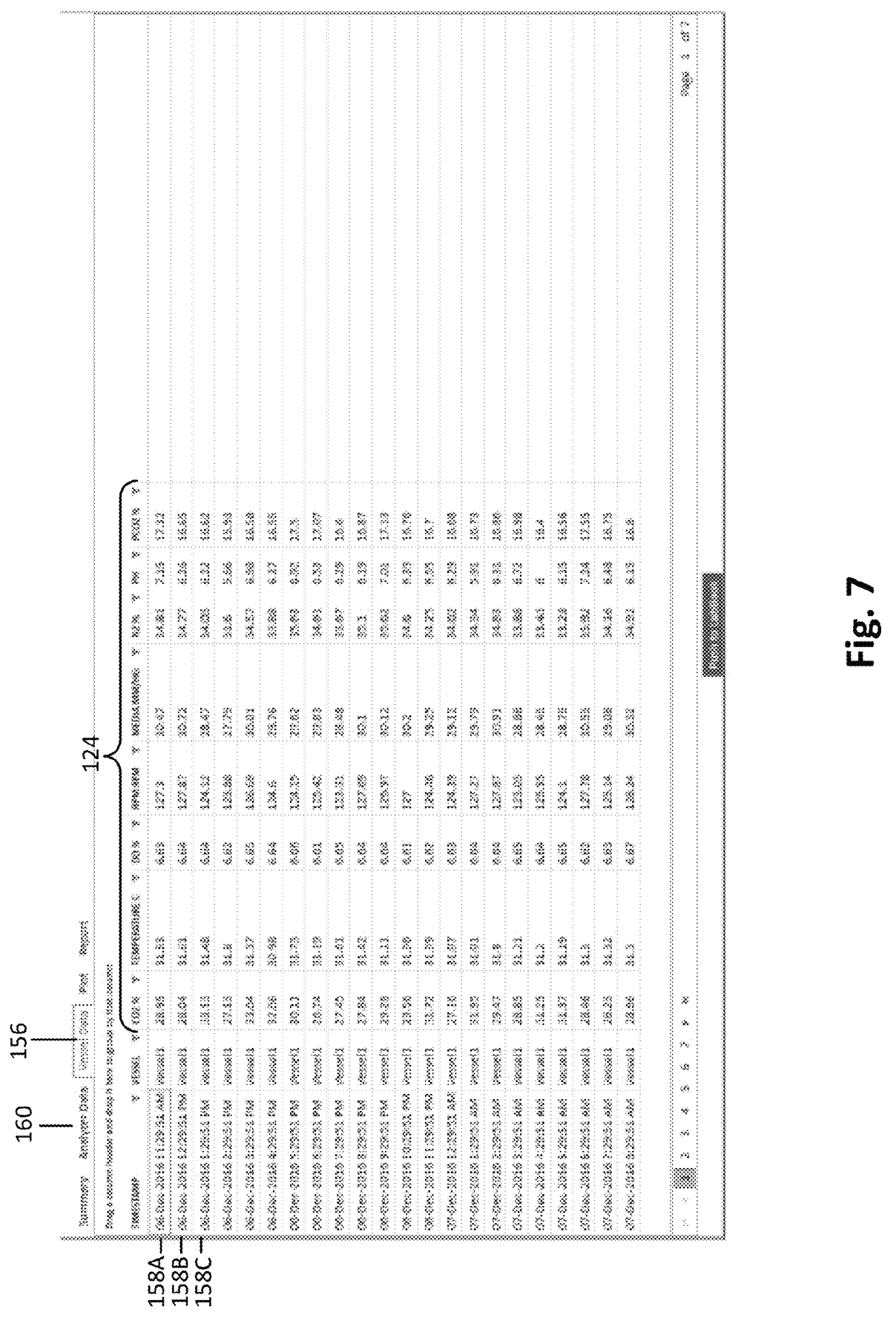

FIG. 7 shows bioreactor data 124 for a single batch that has been averaged over a timespan 153, in accordance with illustrative embodiments of the invention. As shown under the vessel data tab 156, the bioreactor data 124 was collected in a timespan 153 of one-hour intervals. Thus, the first data point 158A shows timestamp 11:29:51 AM, the second data point 158B shows timestamp 12:29:51 PM, the third data point 158C shows timestamp 1:29:51 PM, and so forth in one-hour intervals until the last data point collected.

Bioreactor data 124 may also be referred to as vessel data 124. As described above, the vessel is part of the reactor and contains, for example, the cell culture, protein or chemical reaction.

In some embodiments, the user may select to display multiple batches (e.g., from a single reactor or multiple reactors). The user may select the desired batch data, and the data appears in order. Because of the large quantity of data, the bioreactor data 124 may run for many pages. For example, "Vessel1" data 124 may run from pages 1-4 (selectable at the bottom of the screen), and "Vessel2" data 124 may run from pages 5-7 (also selectable at the bottom of the screen). Additionally, a filter may be applied to the data so that only the desired parameter data is displayed.

Figure 8:
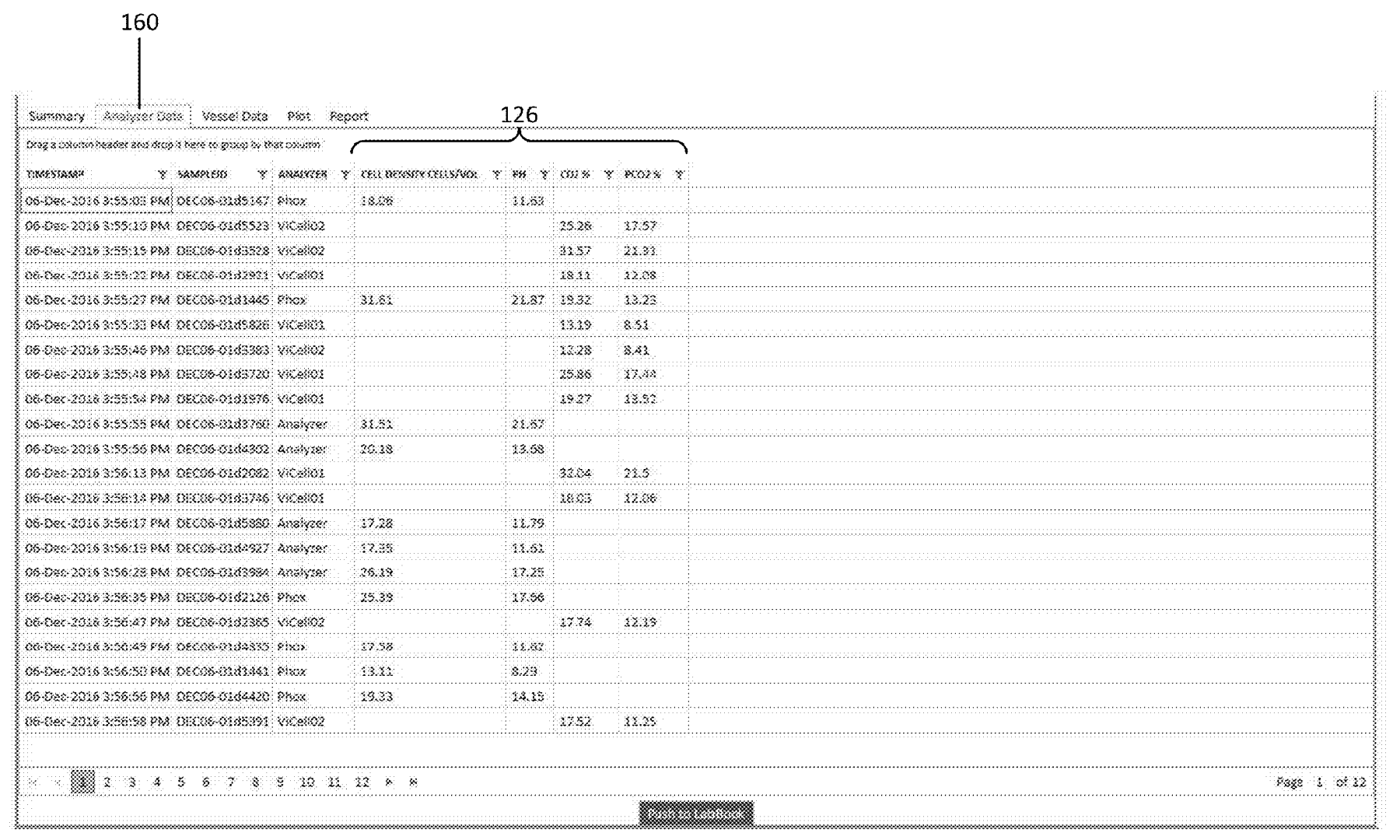

There may also be analyzer data associated with each batch, which was obtained from the sample taken from the analyzer. In some embodiments, the analyzer data can be accessed by clicking the analyzer data tab 160. FIG. 8 shows analyzer data 126 associated with the single batch in FIG. 7. Experiments generally collect analyzer data 126 at discrete intervals over the course of the experiment (e.g., 2-3× a day over 14 days). Thus, in some embodiments, the timespan interval does not apply to analyzer data 126 (i.e., because of the discrete measurement, there is no interval over which to average). As shown, a number of different analyzers are outputting different data 126. For example, the "Phox" and "Analyzer" analyzers intermittently output cell density and pH. In at least one instance, the Phox analyzer also outputs CO2% and PCO2%. ViCell01 and ViCell02 intermittently output CO2% and PCO2%. These four different analyzers have different data output formats. However, they are each connected to the bioprocess management unit, and thus, the data inputs are logged in the system in real-time. Furthermore, any or all of the analyzer data 126 can be used to control the bioreactor operating parameters.

FIG. 9 shows a summary page of selected vessel data 124 and corresponding analyzer data 126. The various measured parameters for the bioreactor (i.e., Vessel1) and the analyzers are shown under the summary tab 166. Statistical data, such as the data max, min, average, and standard deviation may be based on the applied timespan 153. Thus, for example, although the absolute max pH 168 recorded during any sampling period may have been 8.2 over the course of the timespan 153, the displayed maximum pH 168 may be the averaged maximum over the timespan 153. In contrast, in some embodiments the statistical data is not averaged over the timespan 153, and thus, the values achieved (e.g., max, min, etc.) are the values recorded.

Figure 10:
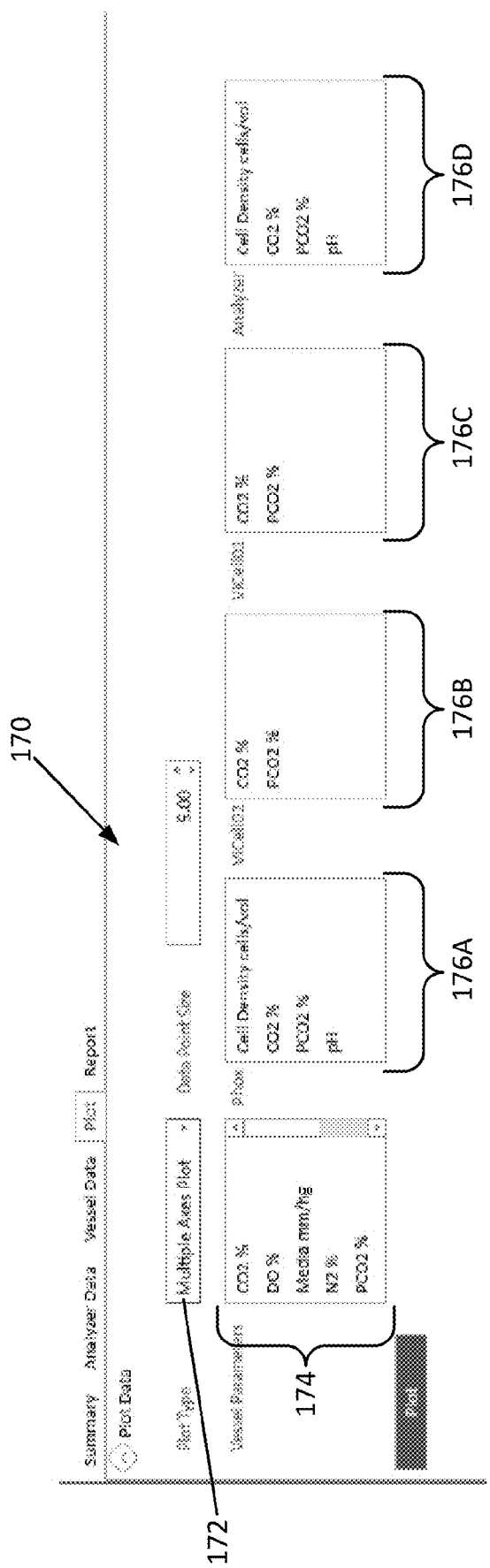
FIG. 10 shows an interface for plotting collected vessel data and corresponding analyzer data, in accordance with illustrative embodiments of the invention.

FIG. 10 shows an interface 170 for plotting collected vessel data and corresponding analyzer data, in accordance with illustrative embodiments of the invention. A variety of graphical plots may be created, for example, multiple axes plots, parameter plots, scatter plots and bubble scatter plots, by selecting the plot type (e.g., from the plot type dropdown menu 172). The interface 170 displays the collected vessel operating parameters 174 for the given batch ID, as well as all of the collected analyzer parameters 176A-D associated with the given batch ID. For example, the Phox analyzer collected data relating to four different parameters 176A of the batch, any and all of which may be selected for plotting.

Figure 11:
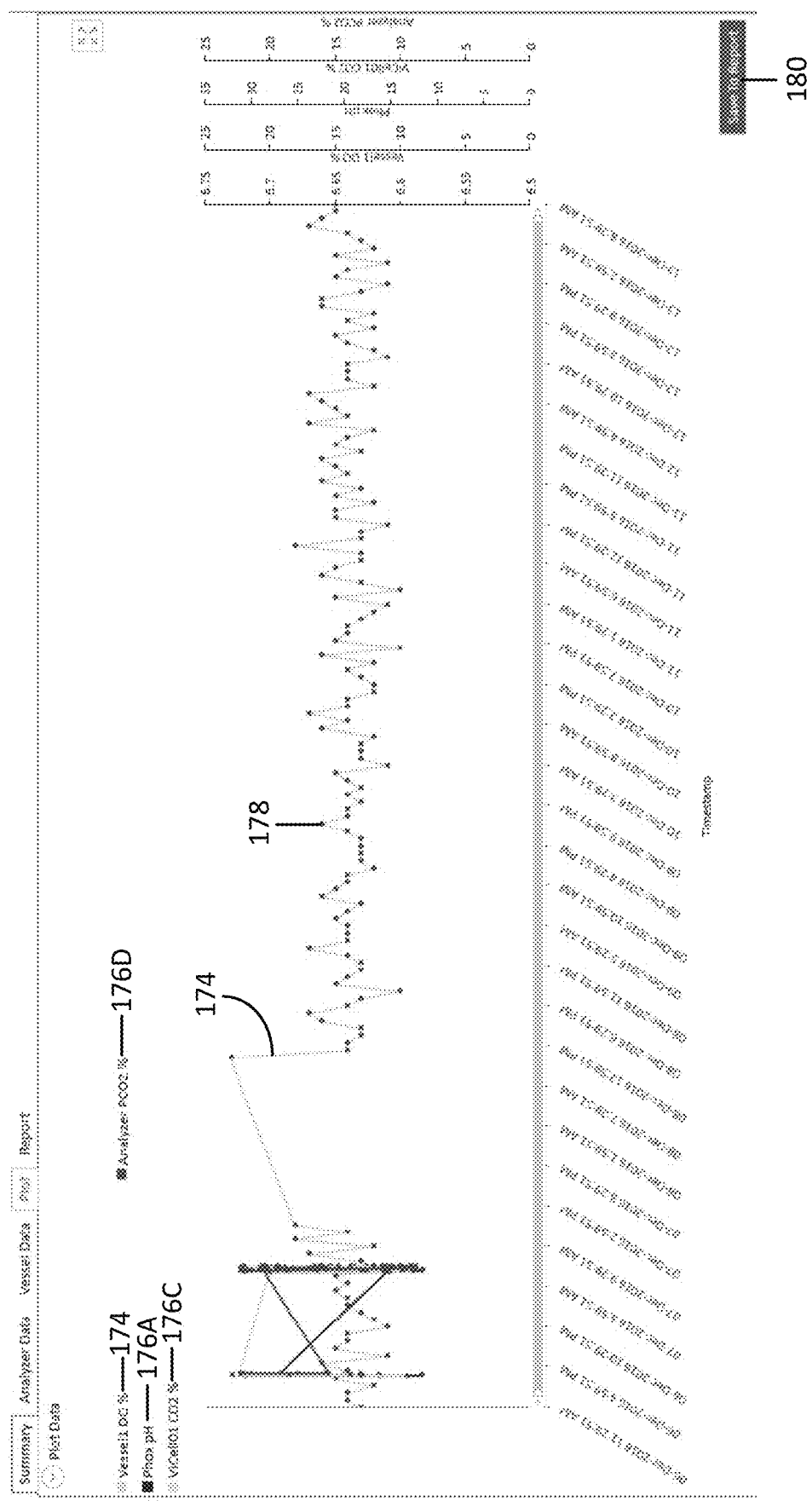
FIG. 11 shows a multiple axes plot comprising vessel data and analyzer data from multiple analyzers, in accordance with illustrative embodiments.

FIG. 11 shows a multiple axes plot comprising vessel data and analyzer data from multiple analyzers in accordance with illustrative embodiments. In this example, the DO % operating parameter 174 from FIG. 10 is selected for the plot. In a corresponding manner, the plot also shows the pH parameter 176A from the Phox analyzer, the CO2% parameter 176C from the ViCell01 analyzer, and the PCO2% parameter 176D from Analyzer. In this plot, no parameter is selected from the ViCell02 analyzer parameters 176B.

In some embodiments the plot is auto-scaled with multiple axes. As shown, the bioreactor operating parameter 174 plot collects data for a longer period of time than the analyzer parameters 176A, 176C-D. This is not uncommon, as vessel data is collected frequently, e.g., in five second intervals over the course of many days. In contrast, analyzer data is generally collected in discrete intervals. As shown, however, vessel data has not been collected every 5 seconds, as indicated by the data point 178. Depending on the zoom and the number of data points, it may be desirable to adjust the size of the data point 178. This can be done by adjusting the data point size drop down menu shown in FIG. 10. Furthermore, the user is able to double click on a point and add notes about the data point 178 that are visible later.

The technician may create reports that are used to adjust the bioreactor operating parameters. Illustrative embodiments have a save to report feature 180 that allows created plots to be automatically integrated into the report. Any notes created on the data points may also be saved in the report.

Figure 12:
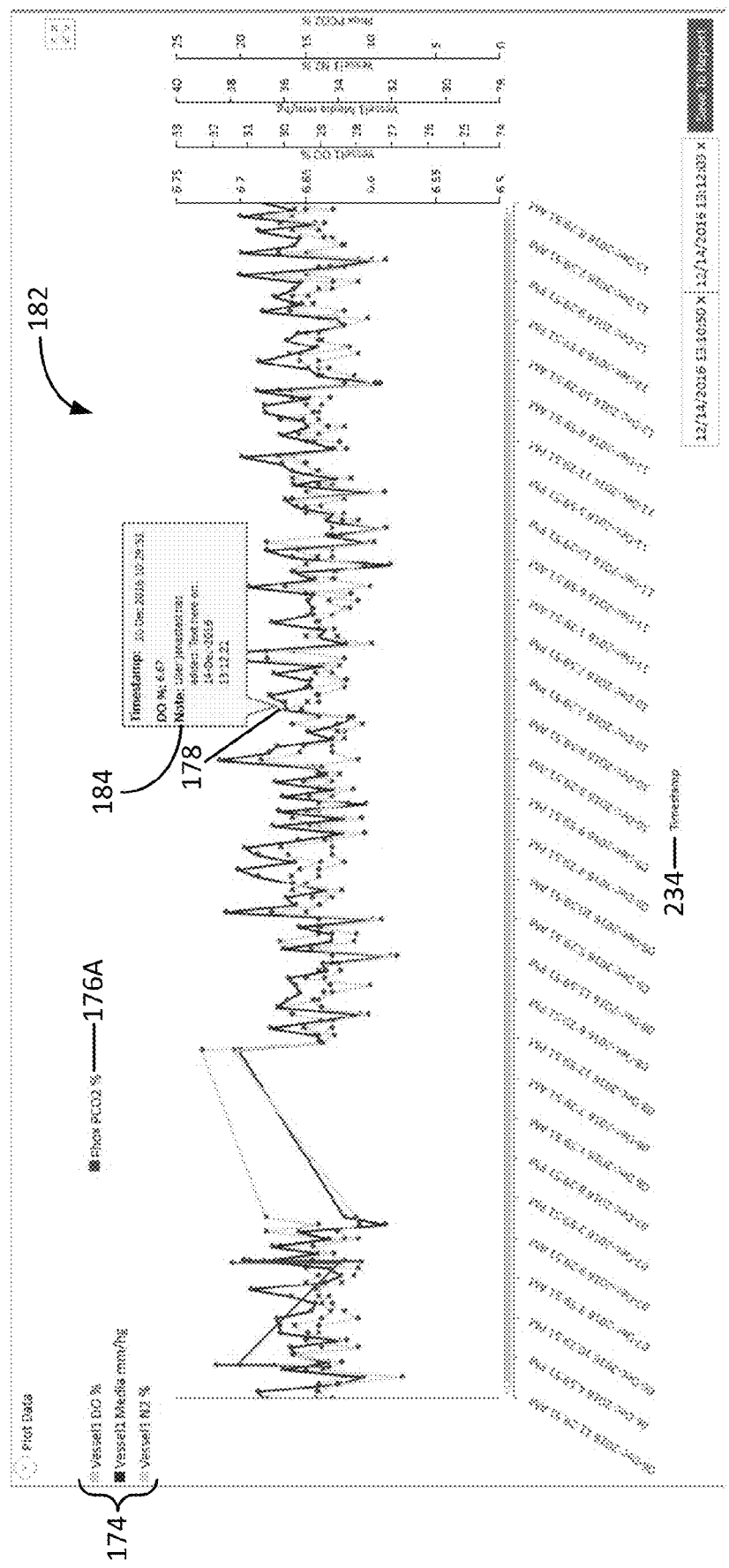
FIG. 12 shows a multiple axes plot comprising three vessel operating parameters and one parameter from an analyzer, in accordance with illustrative embodiments.

FIG. 12 shows a multiple axes plot 182 comprising three vessel operating parameters 174 and one parameter 176A from the Phox analyzer in accordance with illustrative embodiments. As shown, illustrative embodiments may plot more than a single parameter from an independent bioreactor. In a similar manner, more than a single parameter from an independent analyzer may be plotted. Furthermore, in the embodiment shown, the user hovers over the data point 178 with a note 184. When the user hovers over the data point 178 the timestamp 234, parameter value, and note 184 are displayed. In some embodiments, the data point 178 having the note 184 may change colors to help distinguish it from data points 178 not having the note 184.

Figure 13:
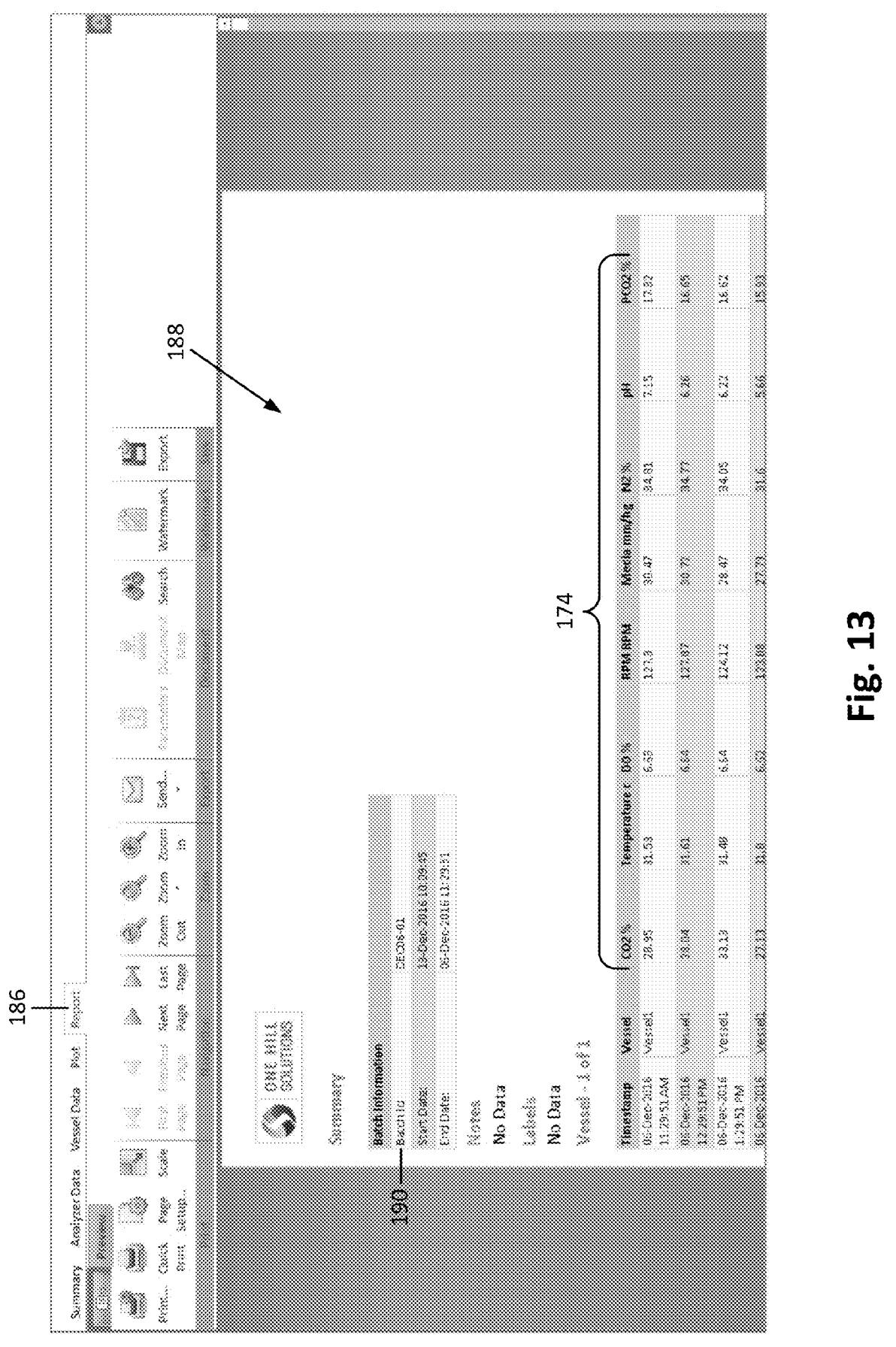

FIG. 13 shows a report 188 generated under the report tab 186. The report tab 186 produces a report 188 of data related to a certain batch ID 190 (e.g., Batch ID DEC06-01). The report 188 can be used to make adjustments to an active bioreactor process, or to make adjustments to parameters in future bioreactor experiments. The report 188 shows all of the data relating to vessel operating parameters 174 and displays it based on the selected timespan. In some other embodiments, the report 188 displays all of the collected data not averaged over the selected timespan.

Figure 14:
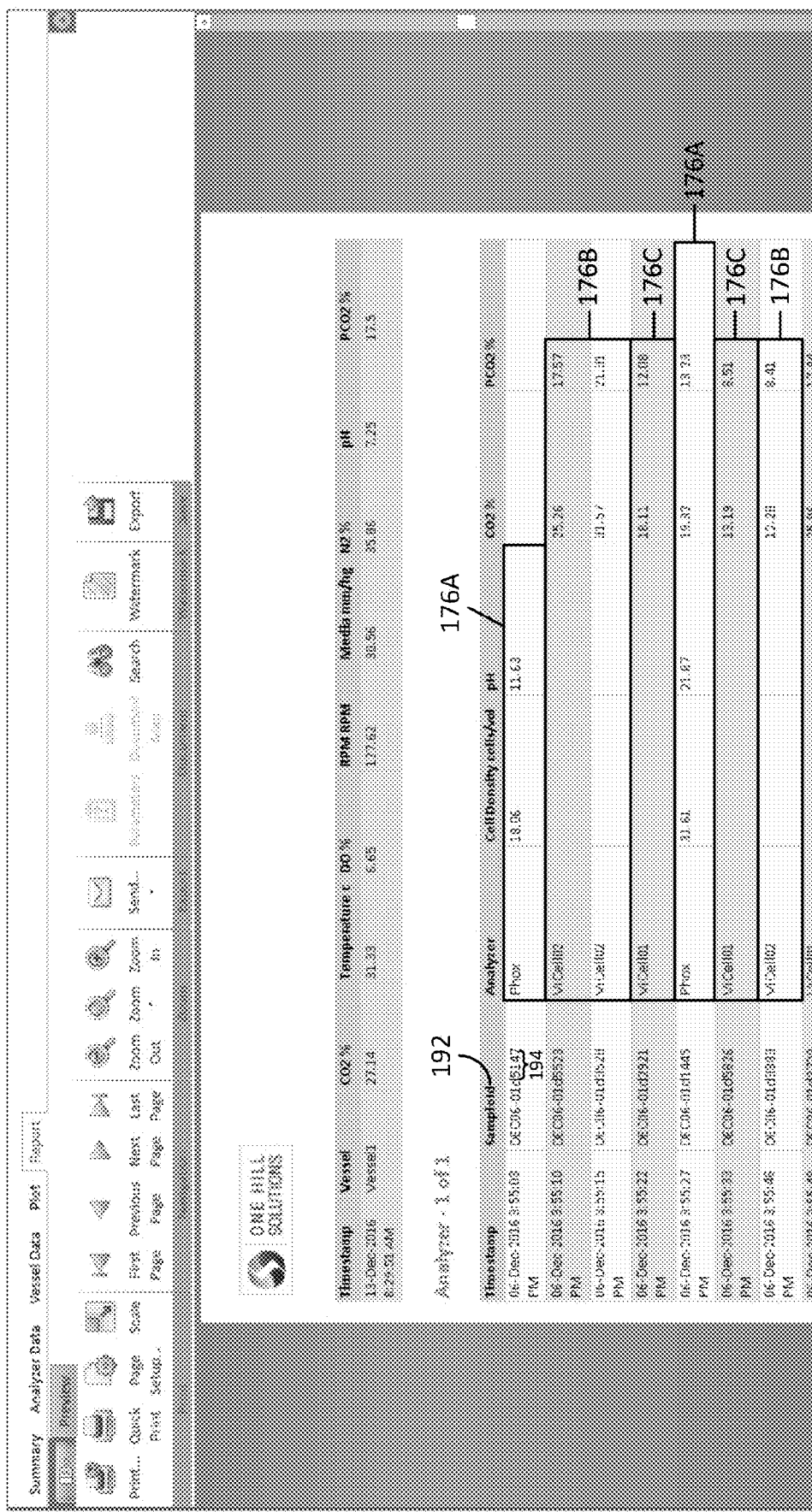
FIG. 14 shows a latter portion of the report generated in FIG. 13.

FIG. 14 shows a latter portion of the report 188 generated in FIG. 13. In this screenshot, all of the analyzer data relating to the selected analyzer parameters 176A-C is shown. Each time analyzer data is collected, it may be assigned a sample ID 192. The sample ID 192 may be, for example, a combination of the batch ID, a delimiter, and a unique portion 194. Each sample ID 192 is associated with a discrete report. Furthermore, each discrete report may have data about different parameters, even if from the same analyzer. The technician can choose what parameters should be tested for with each sample ID 192. For example, a discrete analyzer report having sample ID 192 "DEC06-01d5147" is taken from the Phox analyzer relating to Cell Density and pH parameters 176A. Another discrete analyzer report having sample ID 192 "DEC06-01d1445" is taken from the Phox analyzer relating to Cell Density, pH, CO2% and PCO2% parameters 176A.

Figure 15:
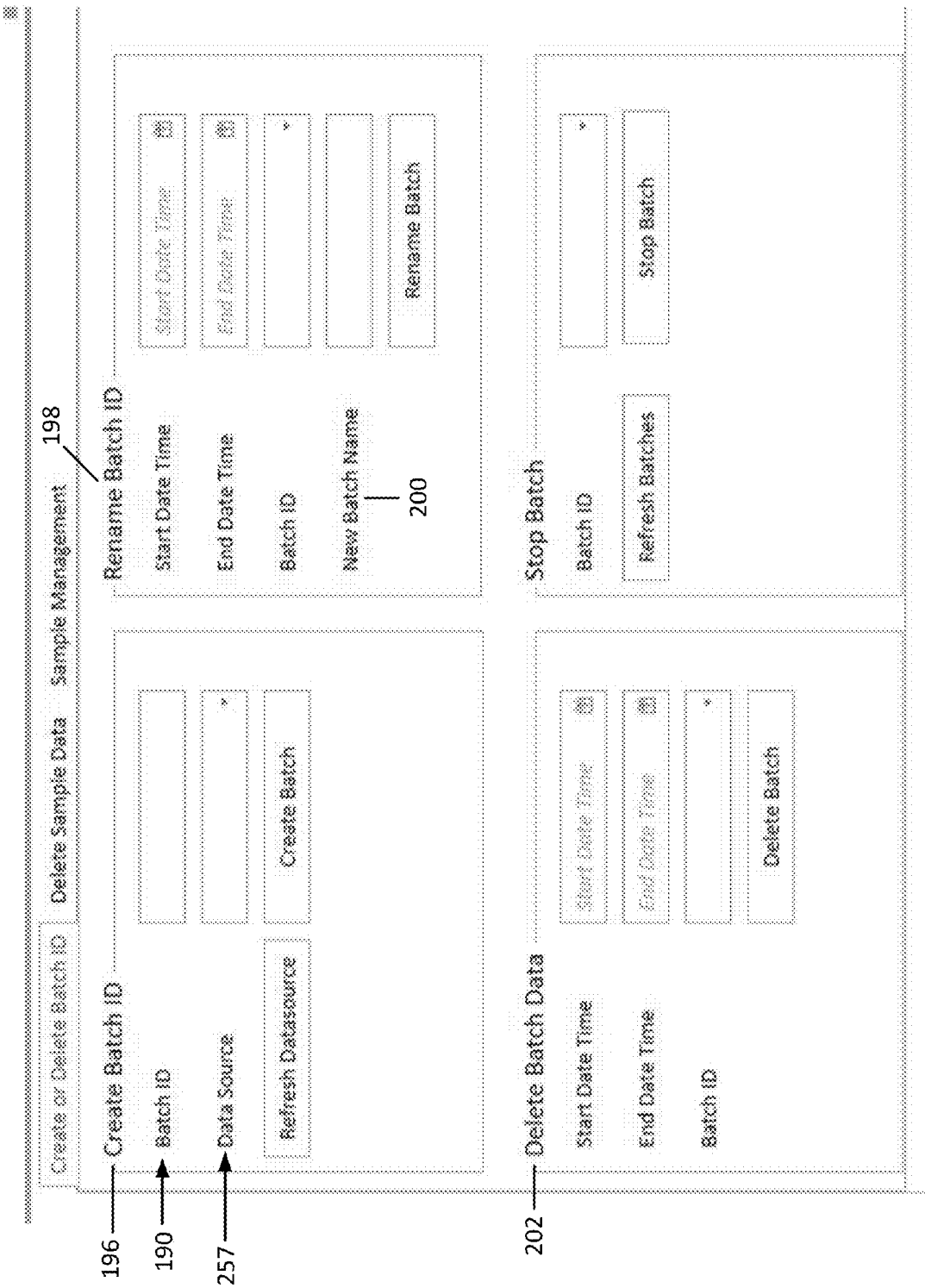
FIG. 15 shows a screen for managing batch ID, in accordance with illustrative embodiments of the invention.

FIG. 15 shows a screen for managing batch ID 190 in accordance with illustrative embodiments of the invention. In some embodiments, the bioreactor creates the batch ID 190. For example, the bioreactor may automatically create the batch ID 190, or the technician may input the batch ID 190 at the bioreactor interface. Illustrative embodiments of the invention have drivers that are configured to obtain the batch ID 190 from the bioreactor.

Alternatively, if no batch ID 190 exists for the bioreactor, the batch ID 190 may be created within a Create Batch ID input field 196. The user may create the new batch ID 190 by entering the desired batch ID 190 name and selecting the data source 257. The data source 257 may be any non-running bioreactor or analyzer that is connected to the system (i.e., not running an active experiment). In some embodiments, creating the batch ID 190 may also start the experiment in the bioreactor.

Batch ID 190 created by the bioreactor or created under the Create Batch ID input field 196 can be renamed using a Rename Batch ID input field 198. Actively running batches and/or complete batches can be renamed. The user can search for batches by date or by batch ID 190. After identifying the batch, the user can enter a new batch name 200. Thus, the new batch name 200 is now associated with the data stored under the old batch ID 190.

Furthermore, the system allows users to search for and delete all associated batch data. As described previously, the user can search for batches by date and/or by batch ID 190. Deleting batch data, (e.g., under a delete batch data 202 input field) deletes all of the collected batch data and may also delete corresponding analyzer data.

The batch management menu may be used to stop the recording of data from currently running batches. In some embodiments, the batch management menu may also stop batches that are currently running on the bioreactor. The user may search for a batch to stop by batch ID 190 and/or by date. However, in some embodiments, the user may only search by batch ID 190. Stopping a batch and/or the recording of data may have serious effects on the experiment. To that end, in some embodiments the system may mitigate accidental stoppage. For example, the user may have to enter their password credentials to stop the recording of data and/or to stop the batch.

FIG. 16 shows a status identifier screen 204 for the bioreactors and the analyzers connected to the bioprocess management unit. Illustrative embodiments show the name, station, status and area (i.e., location) of the connected devices. The status checker 206 indicates whether the devices are connected to the network. All of the connected devices on the network are pinged, and the user is able to determine whether the communication channel is operating. For example, ViCell01 in area Lab2 is shown as not connected (i.e., by Red indicator "R" 208). For example, an Ethernet cord may be disconnected, or perhaps the network is down in Lab2. When a device is disconnected from the bioprocess management unit 122 a text and/or email may be sent advising the user that the device has been disconnected.

Furthermore, as shown, devices in multiple different locations, e.g., rooms, facilities, cities, states, countries, may be connected and controlled in real-time by the bioprocess management unit. It should be understood that receiving, controlling, and processing data in "real-time" includes the time delay caused by the transmission of data and processing of data. For example, the process management unit 122 may be in the United States and some of the bioreactors 102A-102N may be in Europe. Although there is a time delay for the process management unit to receive the data from the bioreactors 102A-102N over a network or plurality of networks, the process is considered to operate in real-time. Furthermore, real-time may include the delay in processing time once the data is received.

Additionally, in illustrative embodiments where a control signal is sent back to the bioreactors 102A-102N, the term "real-time" may include the time it takes to transmit a control signal from the process management unit 122 to the bioreactors 102A-102N. The real-time adjustment of bioreactor operating parameters based on real-time data may enable a feedback loop not enabled by the prior art. For example, the bioreactor operating parameter may be adjusted in real-time based on the bioreactor data and/or the bioanalyzer data collected and correlated in real-time, in order to save the population of cells.

Figure 17:
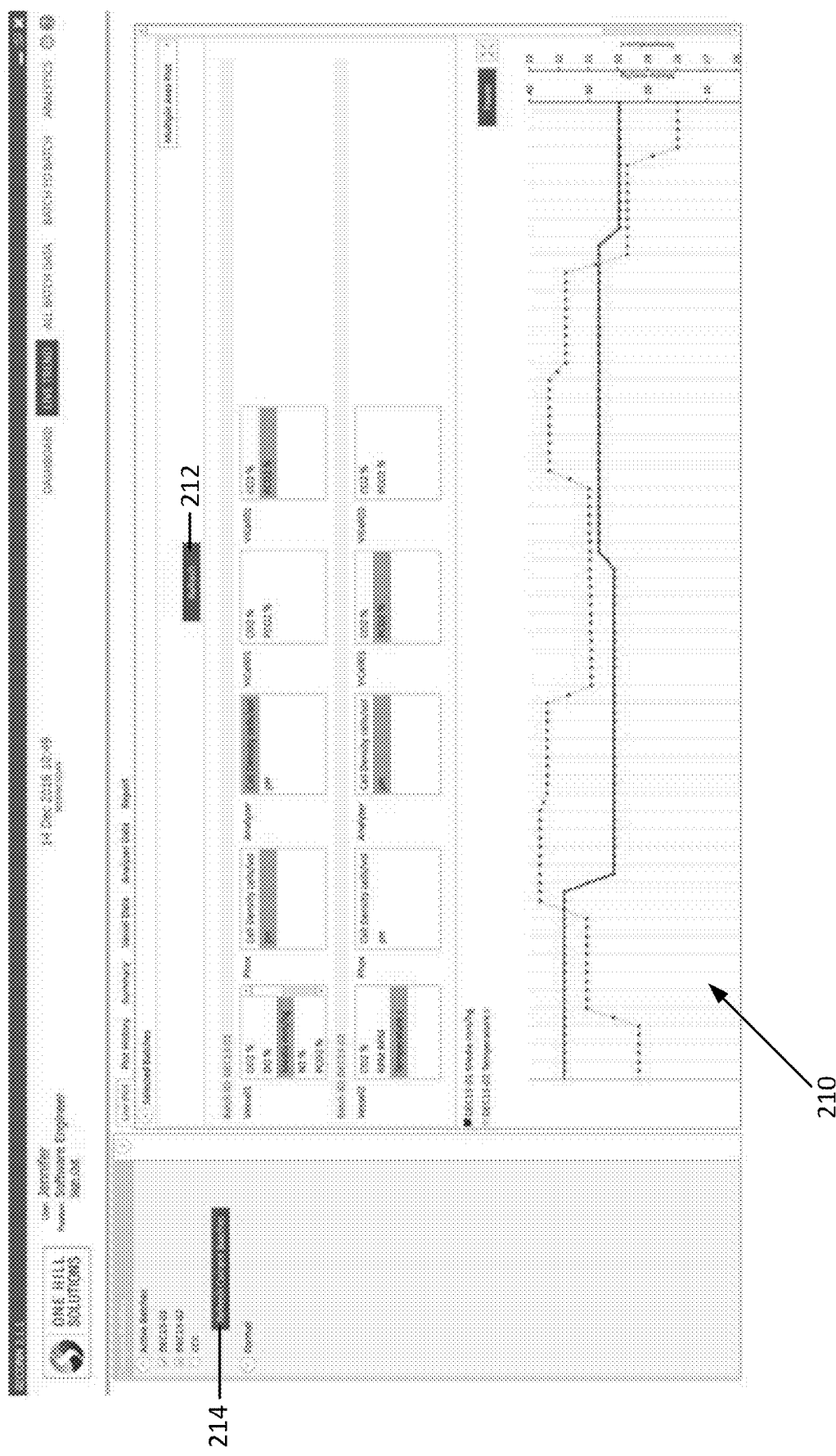
FIG. 17 shows a screen for capturing and monitoring live bioreactor and live analyzer data, in accordance with illustrative embodiments of the invention

FIG. 17 shows a screen for capturing and monitoring live bioreactor and live analyzer data. In illustrative embodiments, the live plot tab shows a live plot 210 of selected bioreactors and/or analyzers. The refresh current batches button 214 refreshes the list of connected/running bioreactors. Technicians can then select which bioreactors (i.e., batches) they wish to see live data for. For example, active batches "DEC13-01" and "DEC13-02" are displayed, but "CCC" is not.

The refresh button 212 refreshes all of the available parameter data available for selected connected batches. Preferably, the refresh interface displays any devices that collected data within a limited period (e.g., the last ten minutes). Thus, the refresh button 212 updates any data sources that have been added or dropped within the limited period. Although illustrative embodiments describe live plots 210, it should be understood that live data and historical data from the plot may be displayed simultaneously. Thus, data from the last ten minutes may be displayed in addition to live data gathered. However, embodiments are not limited to this time period. For example, the live plot 210 can show all of the data collected from the real-time plot, or other intervals of time (e.g., last five minutes). Illustrative embodiments may have a limited period of display in order to reduce the amount of data displayed from large data collection (e.g., multiple parameter plots for data collected every five seconds for the course of many days).

In accordance with illustrative embodiments, FIG. 17 shows that two bioreactors and at least four analyzers are connected to the bioprocess management unit and collected data in the last ten minutes. The bioreactors each have an associated batch ID. Thus, the first bioreactor has batch ID "DEC13-01" and the second bioreactor has batch ID "DEC13-02." As shown, the live plot 210 has two parameter plots: the "Media mm/hg" parameter data from the DEC13-01 batch, and the "Temperature c" parameter data from the DEC12-02 batch. Only two parameter plots are shown for the sake of convenience, however, users may plot all of the available parameters.

The bioprocess management unit also displays the analyzers that have data relating to batch samples. Thus, the four analyzers (Phox, Analyzer, ViCell01, ViCell02 176A-D) have collected associated parameter data for each batch within the last ten minutes. In illustrative embodiments, the analyzers would not show up as a selectable tab if they have not collected data relating to the batch within the last ten minutes.

Figure 18:
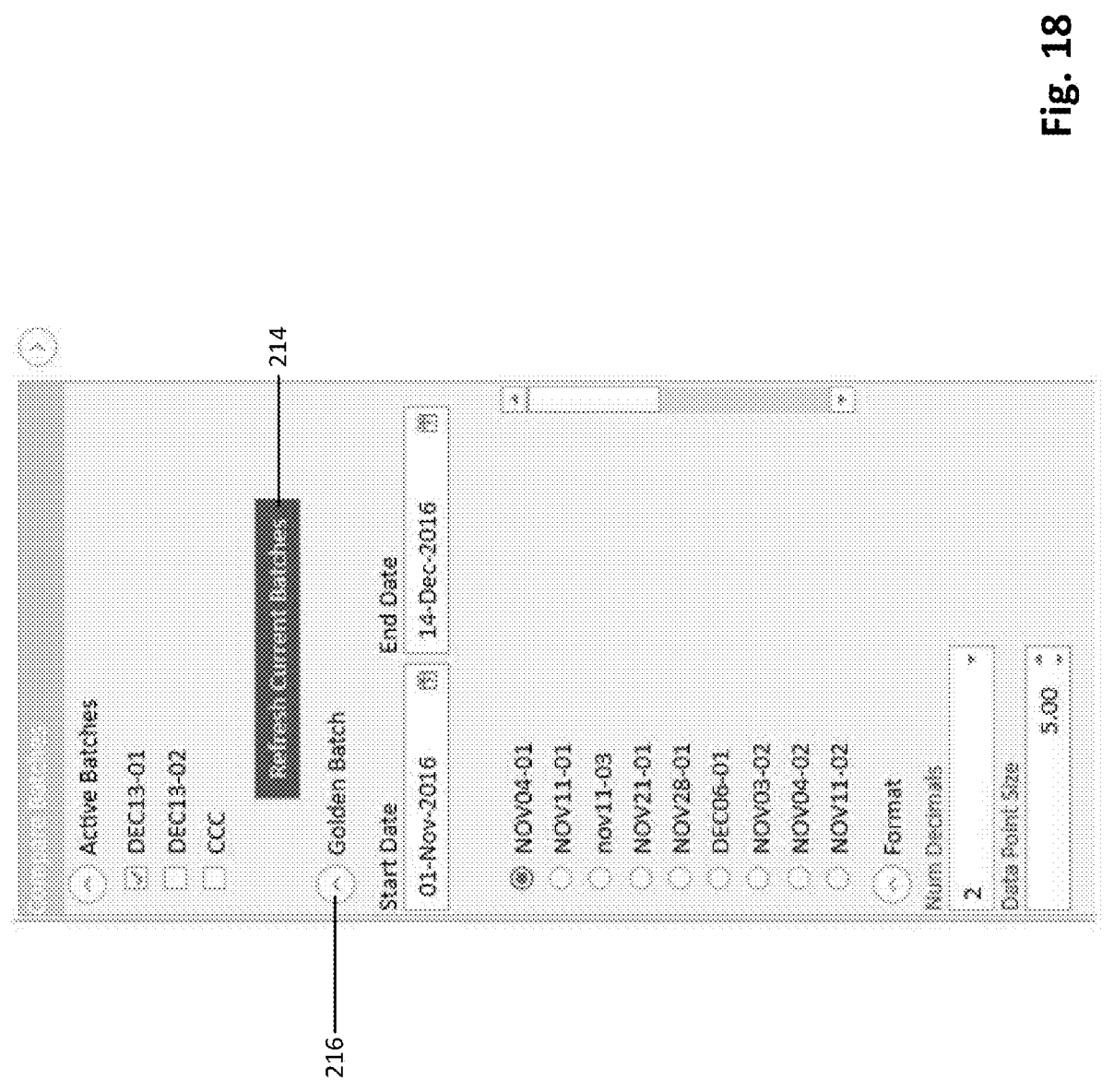

FIG. 18 shows an interface for selecting batches available for plotting. As described above, active batches can be refreshed by selecting the refresh current batches button 214. A golden batch 216 may also be plotted against a live trend (i.e., an active batch). The golden batch 216 is a term used to refer to a completed batch with desirable characteristics. Although illustrative embodiments refer to golden batches 216, it should be understood that any complete plot can be used as a golden batch 216 (e.g., plots that do not have desirable characteristics). Thus, the golden batch 216 can plot simultaneously with the live plot of the active batch, and technicians can draw meaningful comparisons. Furthermore, the bioreactor management unit may (automatically or by user input) adjust the parameters of the live batch bioreactor to more closely match the golden batch 216.

Figure 19:
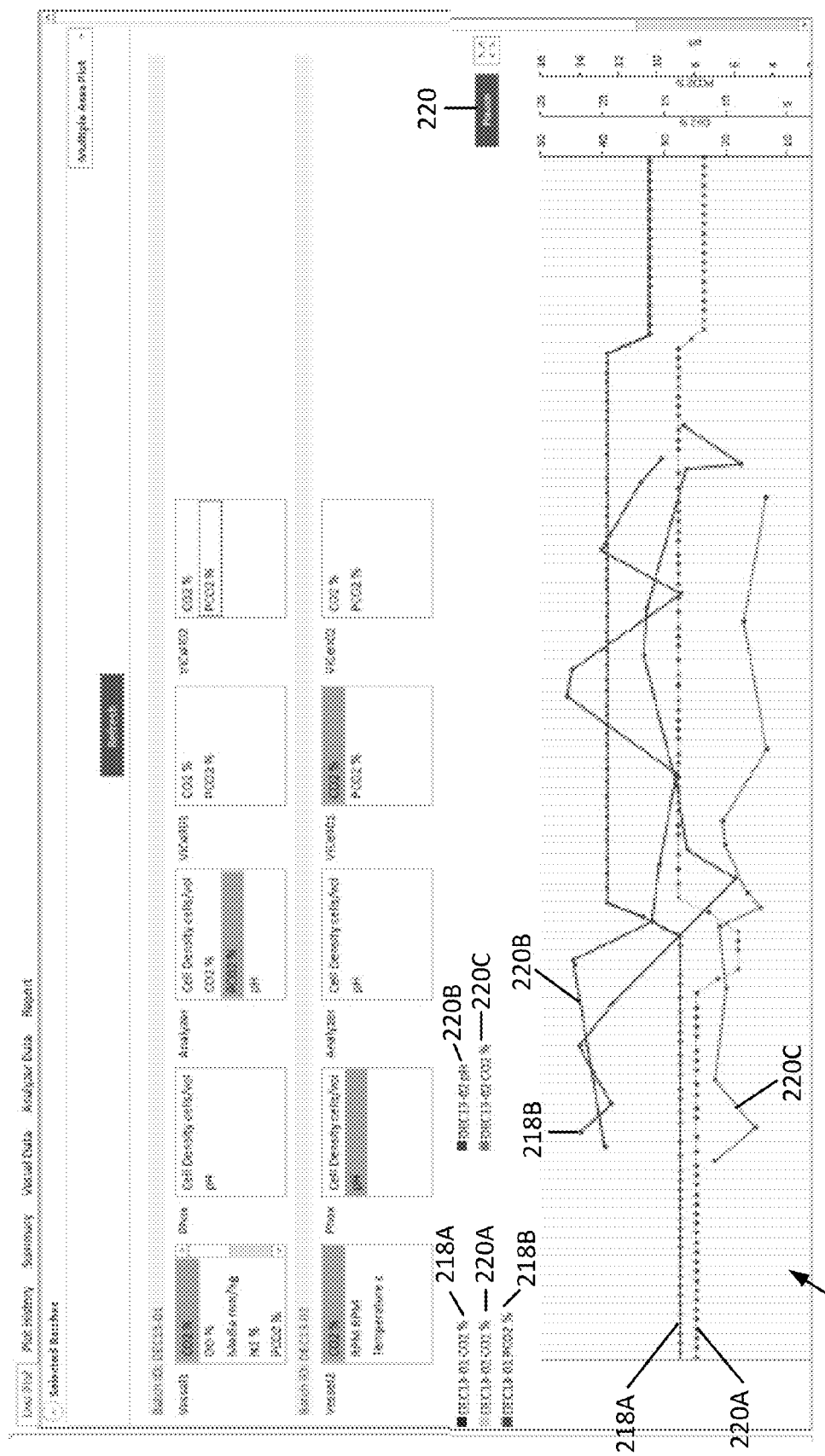
FIG. 19 shows the live plot of a live trend, a golden batch trend, and analyzer trends, in accordance with illustrative embodiments of the invention.

FIG. 19 shows the live plot 210 of a live trend 218A, a golden batch trend 220A, and analyzer trends 218B, 220B, and 220C. The live trend 218A collects live data and plots it in real time. As described above, the golden batch trend 218A data comes from a completed experiment taken at an earlier time. Although the golden batch data was taken at an earlier time, the golden batch trend 220A may plot as if it was started at the same time as the live trend 218A. For example, the golden batch completed two months ago is moved on the time-scale (X-axis) to line up with the start of the current live trend.

Thus, by showing the two trends 218A and 220A as starting at the same time, they can be compared simultaneously. Alternatively, the plots may start at the same time and there may be two x-axis labels. In some embodiments, the X-axis may be extended by some time period to give the technician a visualization of how the golden batch behaves at some time in the future. Accordingly, the technician may adjust parameters based on the later readings of the golden batch.

The analyzer trends 218B, 220B, and 220C may be selected from the available analyzer parameters. These trends 218B, 220B, 220C are shorter than the bioreactor trends because analyzer data 126 collects in discrete intervals, rather than continuously. Thus, in the illustrated trends, the last discrete report was taken at some time prior to the real-time data being collected.

The live plot 210 continuously displays live collected data. To prevent the trend from refreshing, the technician may press the pause button 220. Thus, the live trend on the screen will freeze for further viewing. In some embodiments, once the live trend resumes, it will jump to the current live collected data. Thus, if the pause button 220 is hit for ten minutes and the plot resumes, the live plot 210 will display data recorded ten minutes later.

Figure 20:
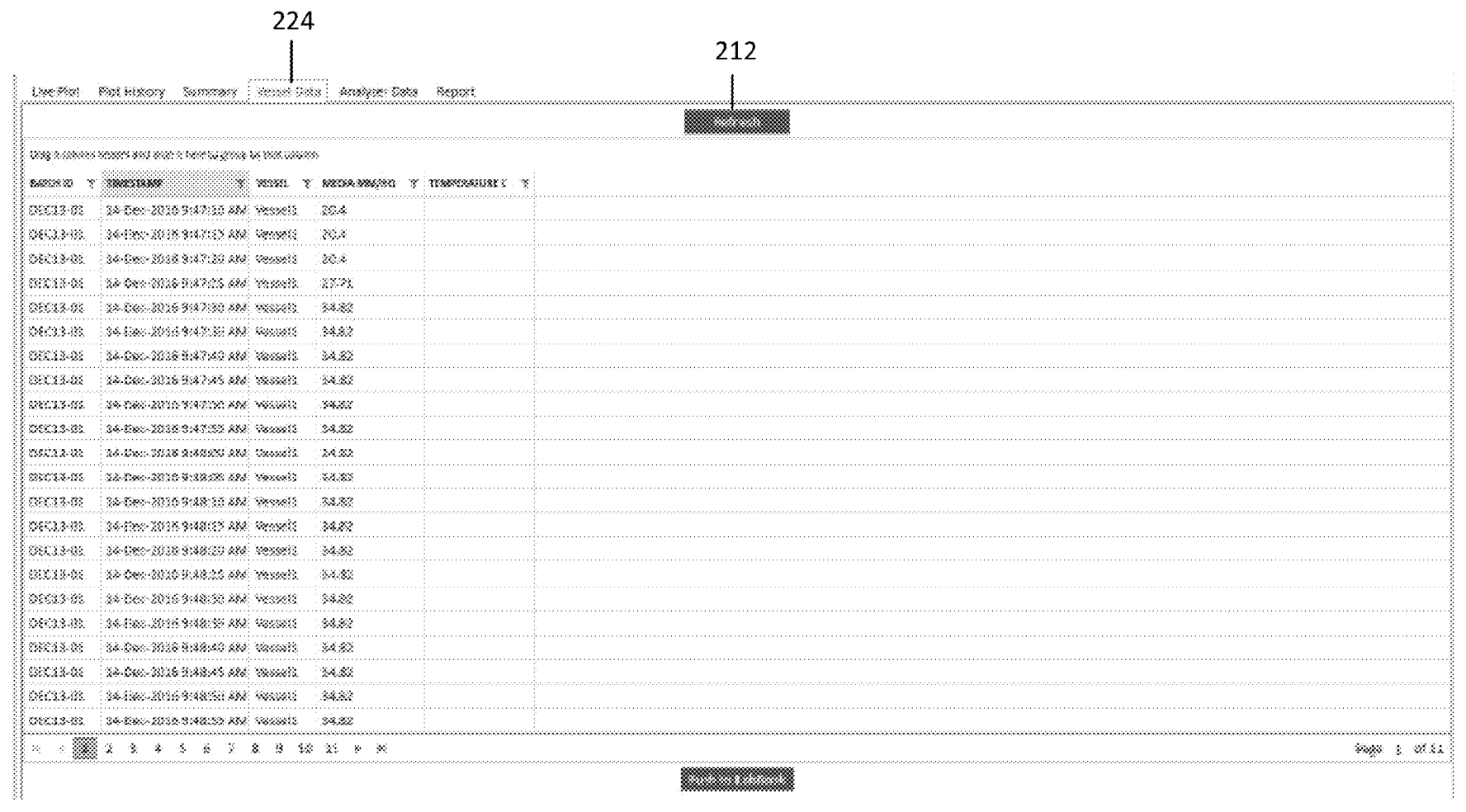

FIG. 20 shows a screenshot of the live bioreactor data displayed in a table format, in accordance with illustrative embodiments of the invention. By selecting the vessel data tab 224, the collected live data is shown. For example, the most recently collected data is shown in five second intervals from vessel1. The data can be updated by hitting the refresh button 212 to show more recently collected data. In some embodiments, all of the collected live data may be shown.

Figure 21:
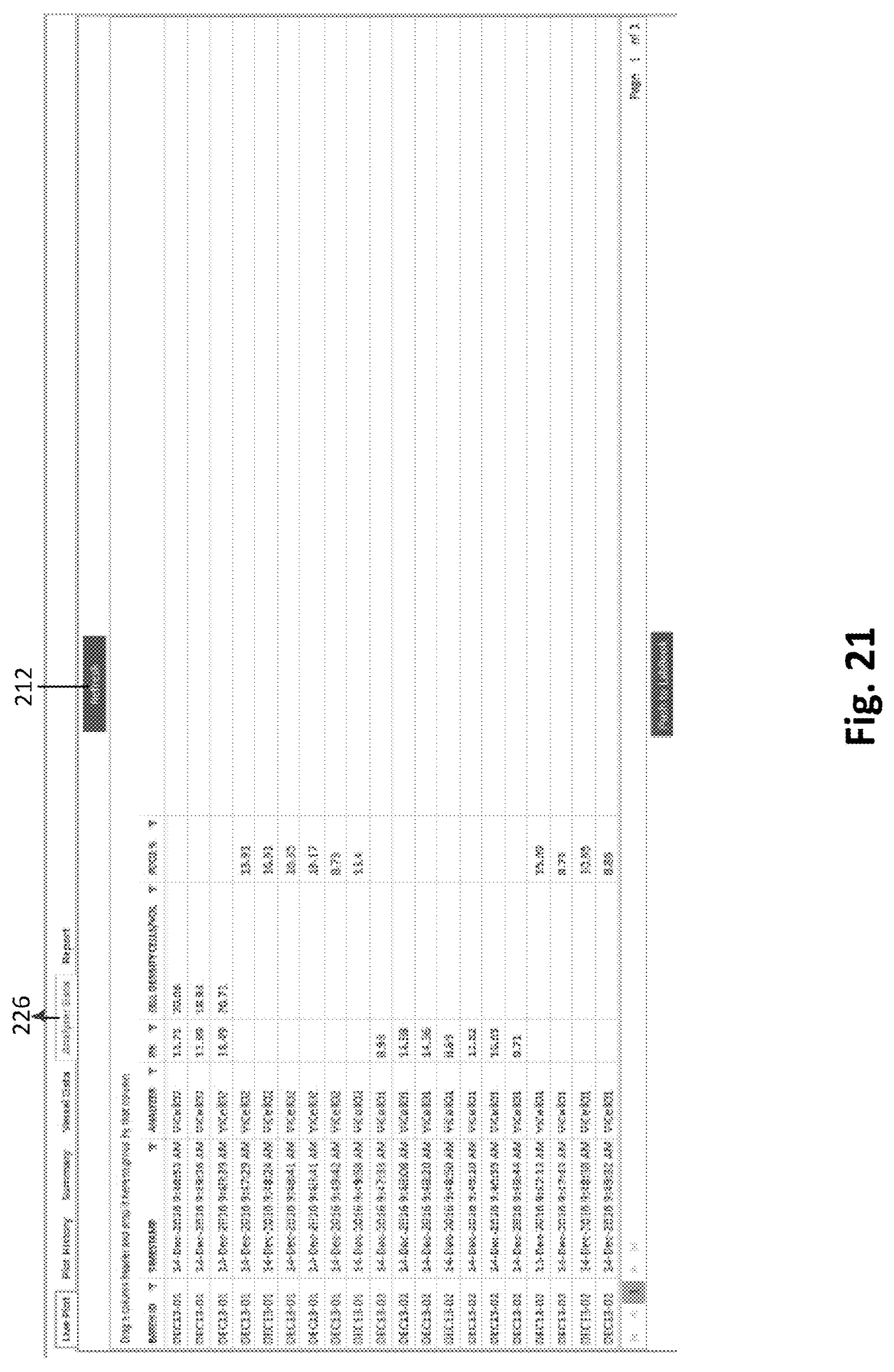

FIG. 21 shows a screenshot of the live analyzer data displayed in a table format, in accordance with illustrative embodiments of the invention. By selecting the analyzer data tab 226, the collected analyzer data is shown. For example, the most recently collected analyzer data is shown based on when the sample was analyzed. This data can be updated by hitting the refresh button 212 to show more recently collected data.

Figure 22:
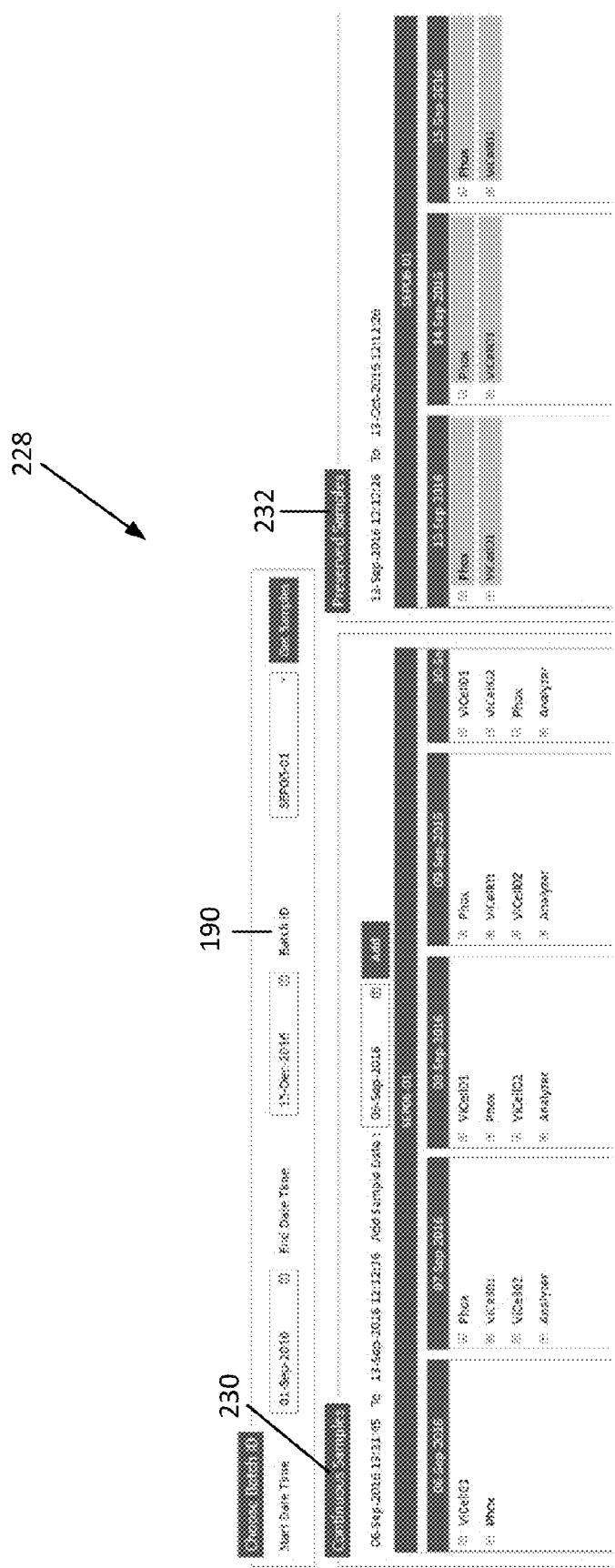
FIG. 22 shows a screenshot of a sample management screen, in accordance with illustrative embodiments of the invention.

FIG. 22 shows a screenshot of a sample management screen 228, in accordance with illustrative embodiments of the invention. Labs may freeze samples taken from the bioreactor prior to running them through the analyzer. The bioprocess management unit automatically collects the data at the time the analyzer is run, and it is unaware of when the sample was drawn from the vessel. For example, a sample may be drawn and stored in a freezer for a period of time before it is tested in the analyzer. The user may move any sample data gathered from a later date to an earlier date for comparison. The date the sample was drawn may be manually entered, and the bioprocess management unit moves the timestamp of the sample data to the time it was drawn.

The batch with the frozen sample may be identified by date or batch ID 190. After an appropriate batch ID 190 is determined, continuous samples 230 and preserved samples 232 are shown. The continuous samples 230 are samples that were tested when the batch was active. The preserved samples 232 are samples that fall outside the start and end date of the batch. The technician can also add the sample date if the date is not available on the timeline.

The data may be grouped by analyzer name to facilitate ease of use. Users may simply drag and drop analyzer data to the appropriate date slot, and may manually enter the time of sample. In some embodiments, a safeguard exists to prevent from data tampering. An audit trail pops up and requires that the user enter password credentials and requires a statement regarding the reason for the change of sample date. If the user cancels the change, the form is reset and all unsaved changes are discarded.

Figure 23:
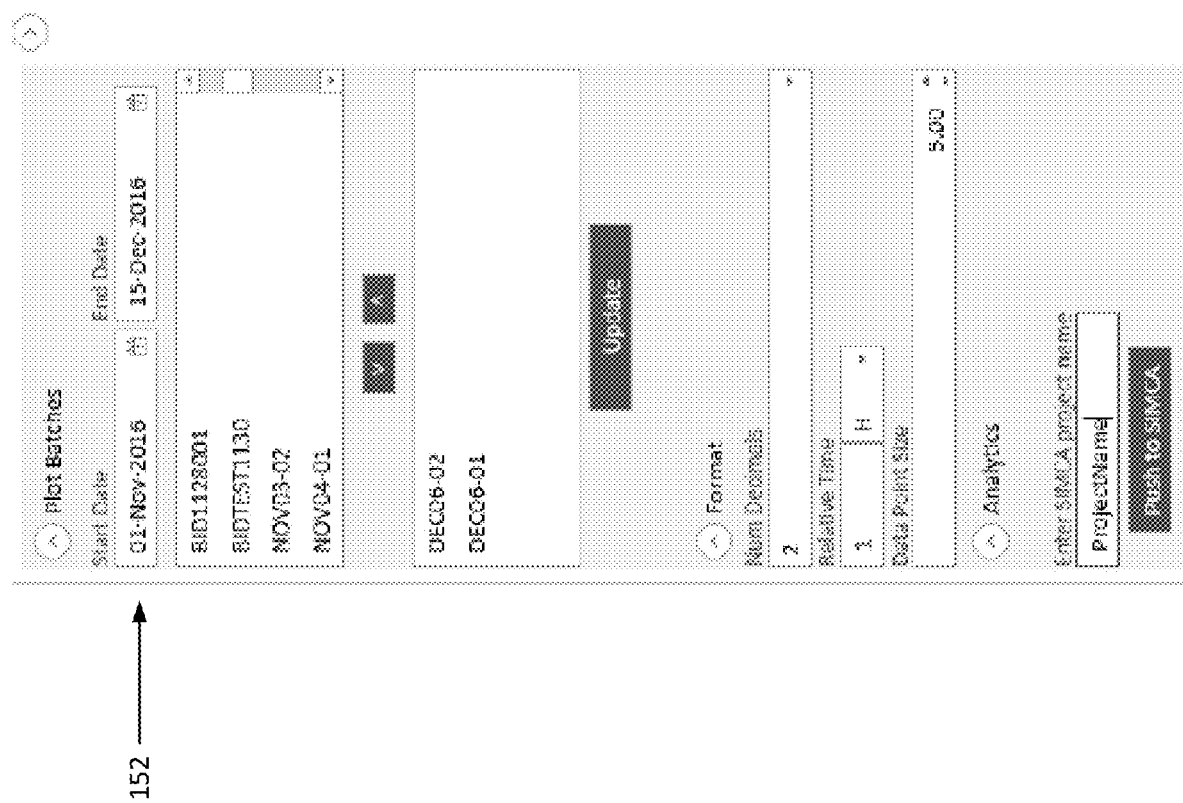
FIG. 23 shows a screenshot of a panel for comparing data from complete batches, in accordance with illustrative embodiments of the invention.

FIG. 23 shows a screenshot of a panel for comparing data from complete batches, in accordance with illustrative embodiments of the invention. As described throughout the application, users may search for batches to compare in the search tab 152. For example, batch "DEC06-02" and "DEC06-01" are selected for comparison.

Figure 24:
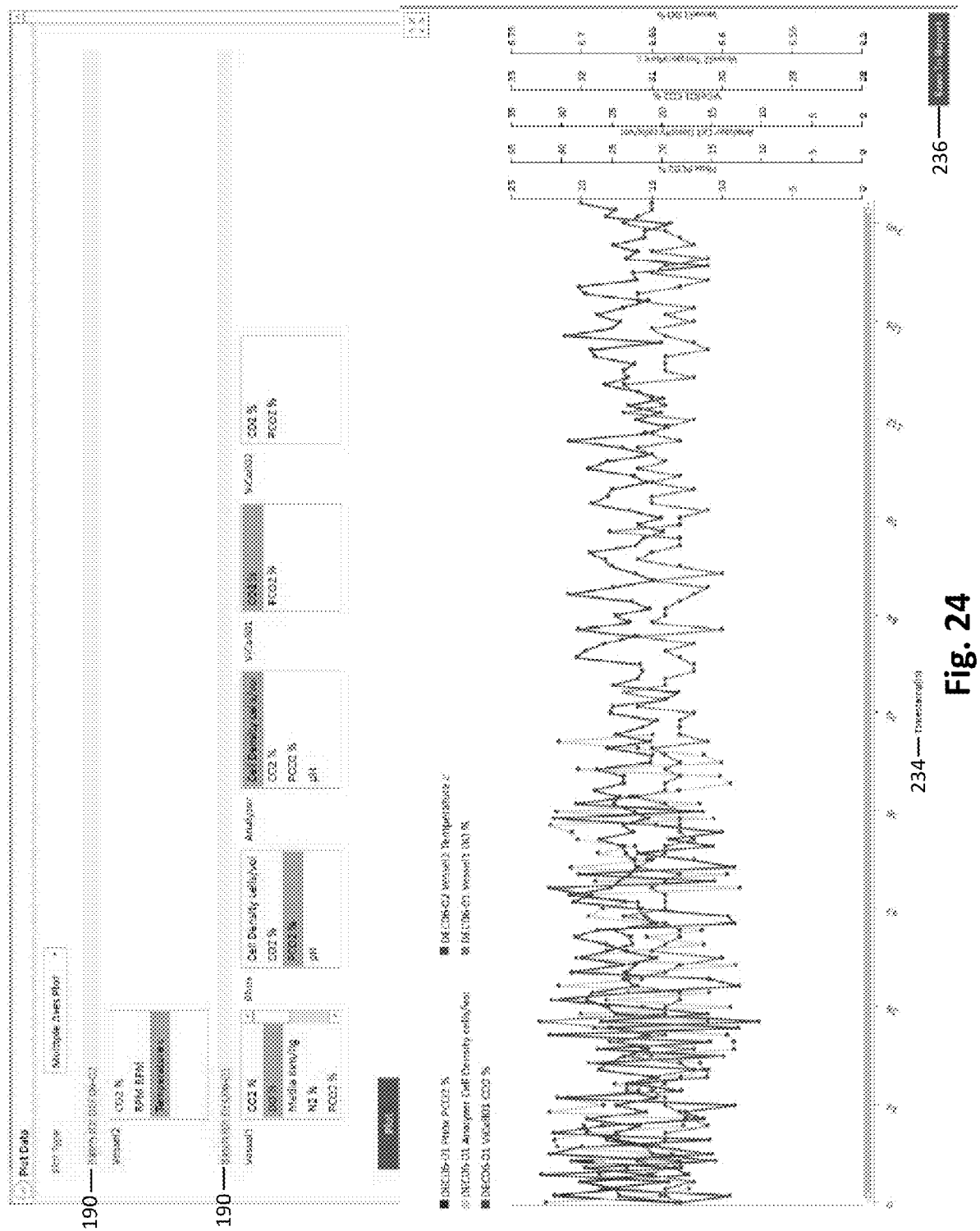
FIG. 24 shows a screenshot of a graph comparing two completed batches, in accordance with illustrative embodiments of the invention.

FIG. 24 shows a screenshot of a graph comparing two completed batches, in accordance with illustrative embodiments of the invention. The data parameters collected for each batch ID 190 are shown and available for plotting. The user may select a plurality of parameters for plotting from each batch, including data collected by the bioreactors and analyzers. Each selected parameter is labeled with a color in the legend. Each parameter is shown on the Y-axis and the timestamps 234 are labeled along the X-axis. Each plot may be saved to a report by clicking the save to report button 236.

Although both batch IDs 190 indicate that they start on DEC06, they may have started at different times. In some embodiments, the system lines up the plots (i.e., the plots start at the same time on the X-axis). Furthermore, the timestamp 234 may indicate the duration of the experiment (e.g., in hours). These plots may also have the aforementioned note functionality. It should be understood that in illustrative embodiments the various functionalities (e.g., the note functionality, the search function) described with reference to either live plots 210 and completed plots are interchangeable.

FIGS. 25-31 show analytics functionality in accordance with illustrative embodiments.

Figure 25:
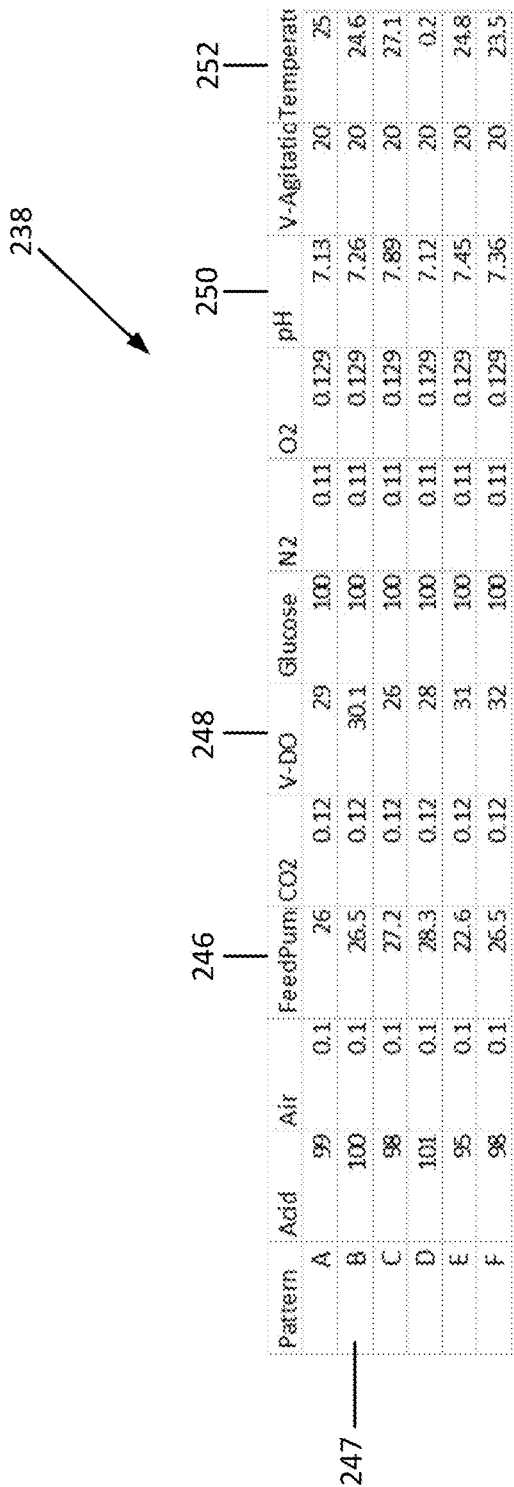
FIG. 25 shows a spreadsheet containing a number of parameters, in accordance with illustrative embodiments of the invention.

FIG. 25 shows a spreadsheet 238 containing a number of parameters, in accordance with illustrative embodiments of the invention. This spreadsheet may come from commercial data analysis software (such as JMP from SAS). Each set of parameters is referred to as a pattern. Pattern B 247 has template values for the various bioreactor operating parameters. For example, a feed pump 246 parameter is set at 26.5, a V-DO parameter 248 is set at 30.1, a pH parameter 250 is set at 7.26, and a temperature parameter 252 is set at 24.6. Illustrative embodiments of the invention may take sets of parameters (e.g., from the spreadsheet 238) and use them as a template for operation of a new batch, which is shown in FIG. 26.

Figure 26:
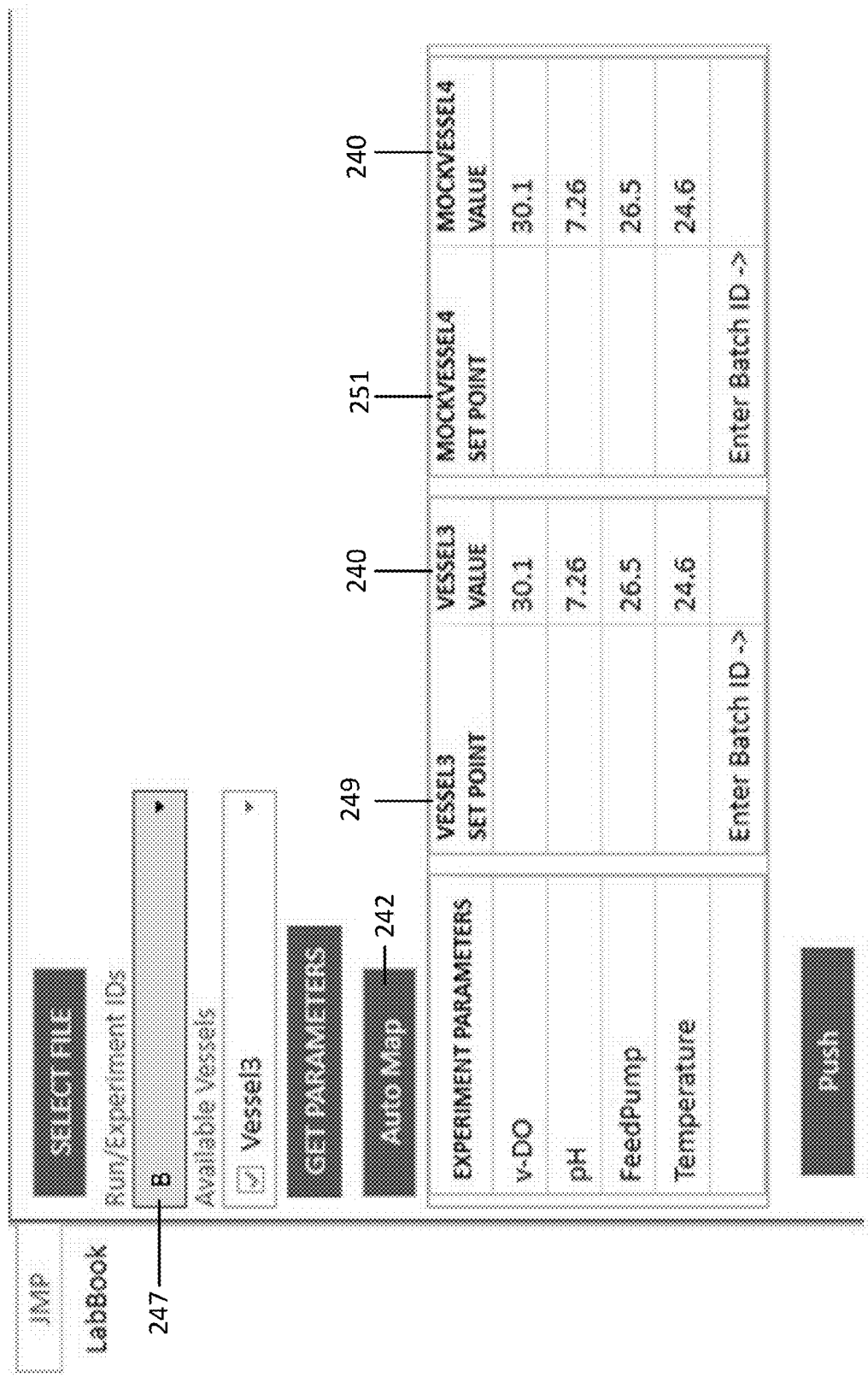
FIG. 26 shows an interface for setting bioreactor operating parameters based on the parameter templates in FIG. 25.

FIG. 26 shows an interface for setting bioreactor operating parameters based on the parameter templates in FIG. 25. The bioreactor operating parameters are the parameters that the bioreactor is configured to collect and/or operate at. As shown, Pattern B 247 from FIG. 25 is selected, which automatically sets the bioreactor operating parameter set point values 240 based on the applicable parameter values from Pattern B 247. The user then selects a connected bioreactor to apply the parameter template. As shown, vessel3 249 and mockvessel4 251 are selected. The user may automatically transfer the set point values 240 from the spread sheet to the selected bioreactor by selecting automap 242. However, the values 240 are user adjustable, in case some changes are preferred from the template.

Figure 27:
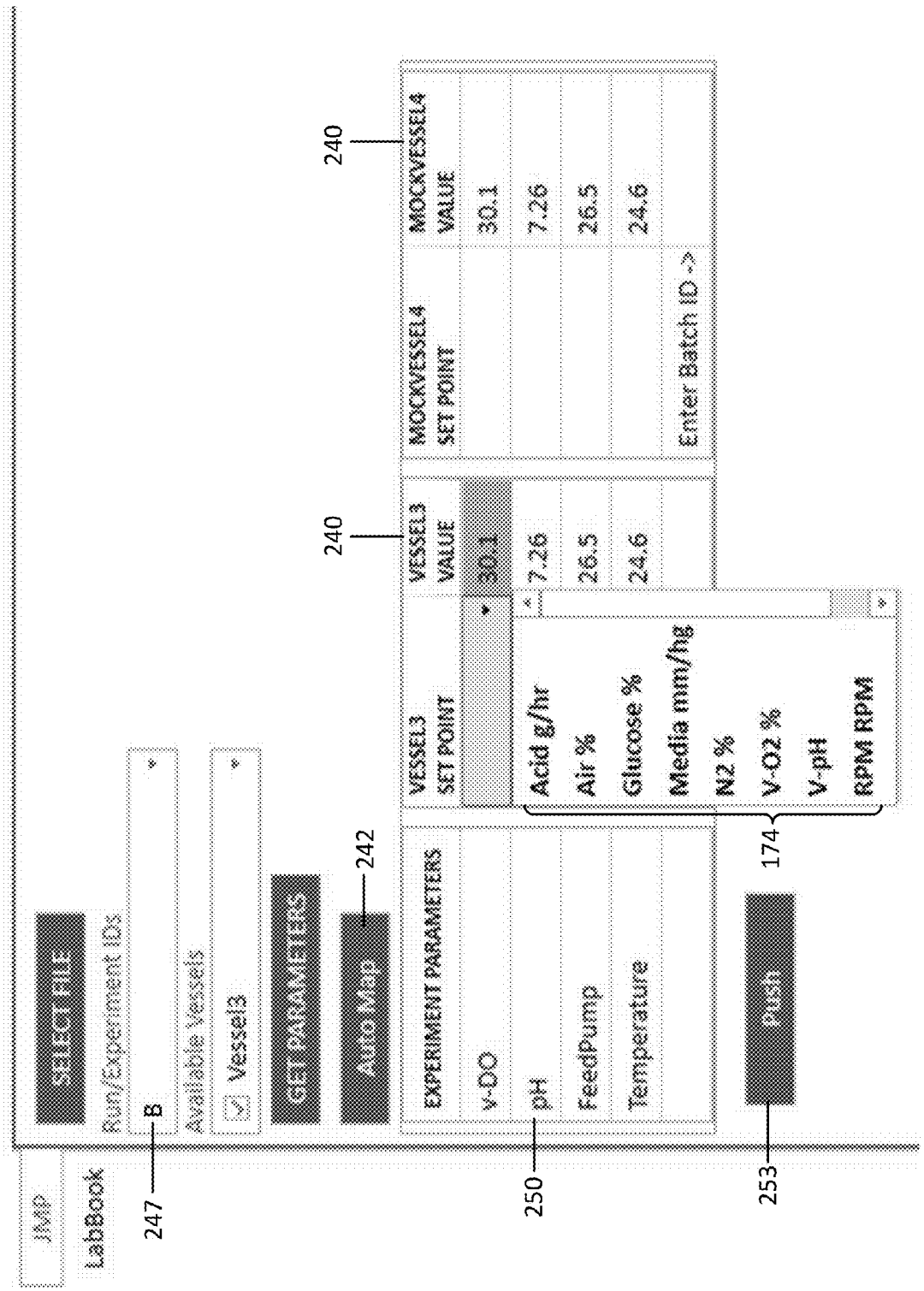
FIG. 27 shows an interface where the user may adjust the template parameter values, in accordance with illustrative embodiments of the invention.

FIG. 27 shows an interface where the user may adjust the template parameter values. For example, a parameter value from Pattern B 247 of the spreadsheet is pH parameter 250. The bioreactor logic may be configured to have the pH parameter 250 named "V-pH." Automap 242 may automatically set the pH parameter 250 value to the V-pH parameter. If incorrect parameters were automapped, no parameter was found, or an entirely different parameter is desired, the user may manually select the parameter from the vessel operating parameters 174 available. Users are also prompted to enter a batch ID for the bioreactor. Once the user hits push 253, the bioreactor may begin the experiment with the set parameter values 240.

Figure 28:
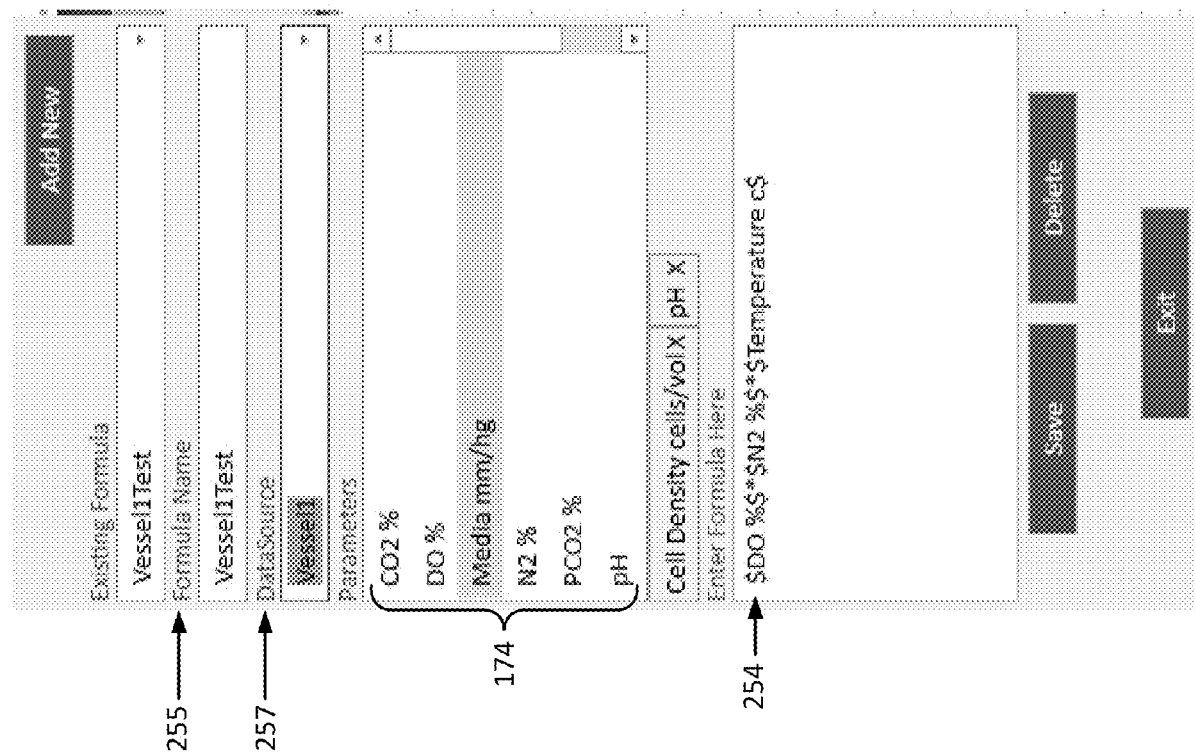
FIG. 28 shows an interface for creating formulas. The user can create a new formula or select an existing formula to modify, in accordance with illustrative embodiments of the invention.

FIG. 28 shows an interface for creating formulas 254. The user can create a new formula or select an existing formula to modify. The formula 254 performs calculations based on selected bioreactor operating parameters 174 and/or analyzer data. The selected formula name is displayed in the formula name field 255. The user can select a data source 257, in this example, Vessel1. Vessel1 has its own set of bioreactor operating parameters 174. It should be noted that the selected data source is the device, and not the batch. The data source may be the bioreactor or the analyzer.

Each data source 257 has configured parameter options that are displayed. In this example, Vessel1 has the ability to collect data related to a number of bioreactor operating parameters 174 options. The user may select more than one data source 257 and/or parameter 174 when creating the formula 254. If the user clicks on the parameter type, it will automatically format and insert into the formula 254 text box. The user may save or delete the formula 254.

Figure 29:
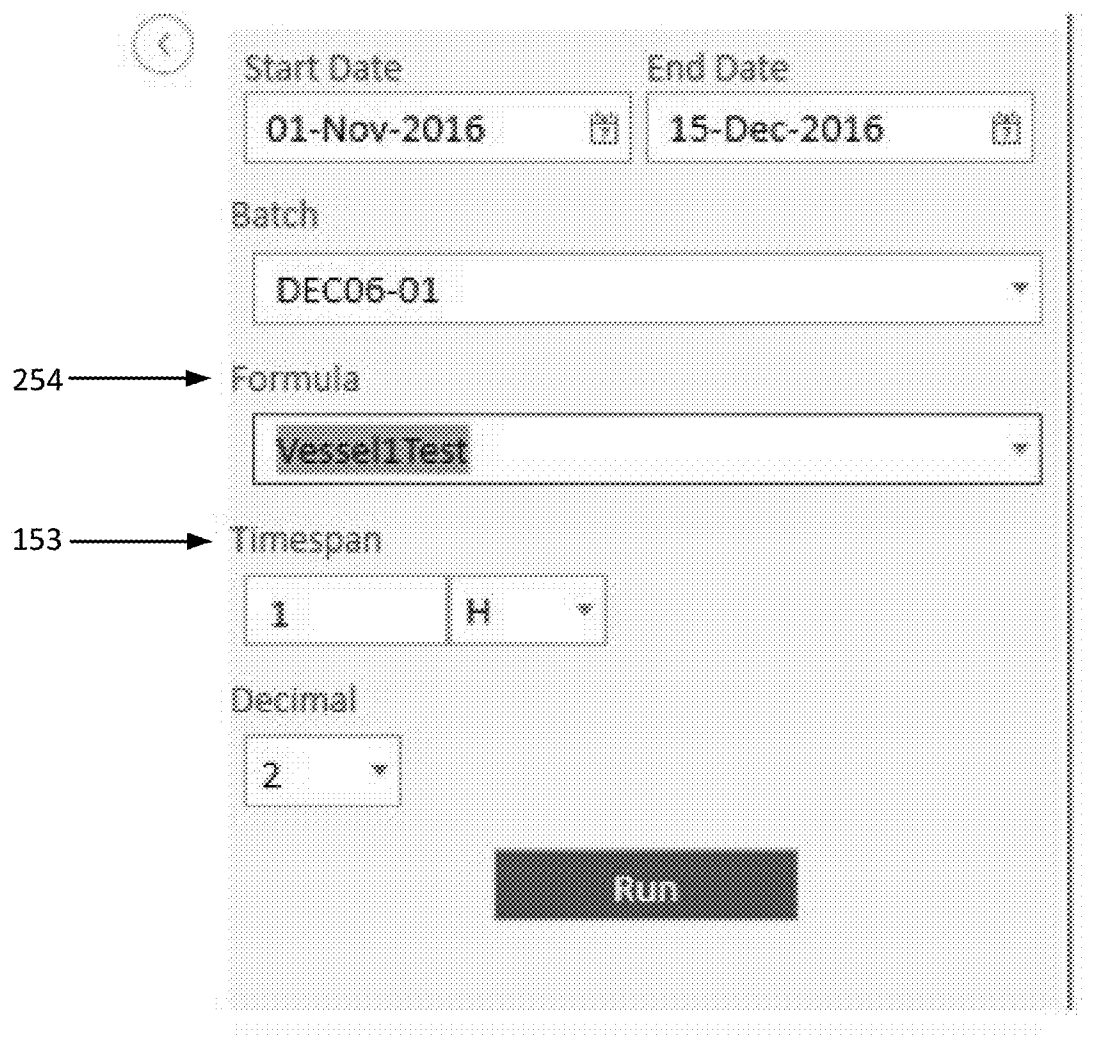

FIG. 29 shows an interface for using a formula 254 to perform calculations on the collected data, in accordance with illustrative embodiments. As shown, batch DEC06-01 has the Vessel1Test formula 254 applied. Although the formula name says Vessel1Test, it is not necessary that the batch run on bioreactor Vessel1 of FIG. 28. This is merely a naming convention for the formula 254. As described previously, the interface has a timespan 153 selection. The data from the selected batch will be averaged over the timespan 153 selected, and the formula 254 may use the averaged data.

Figure 30:
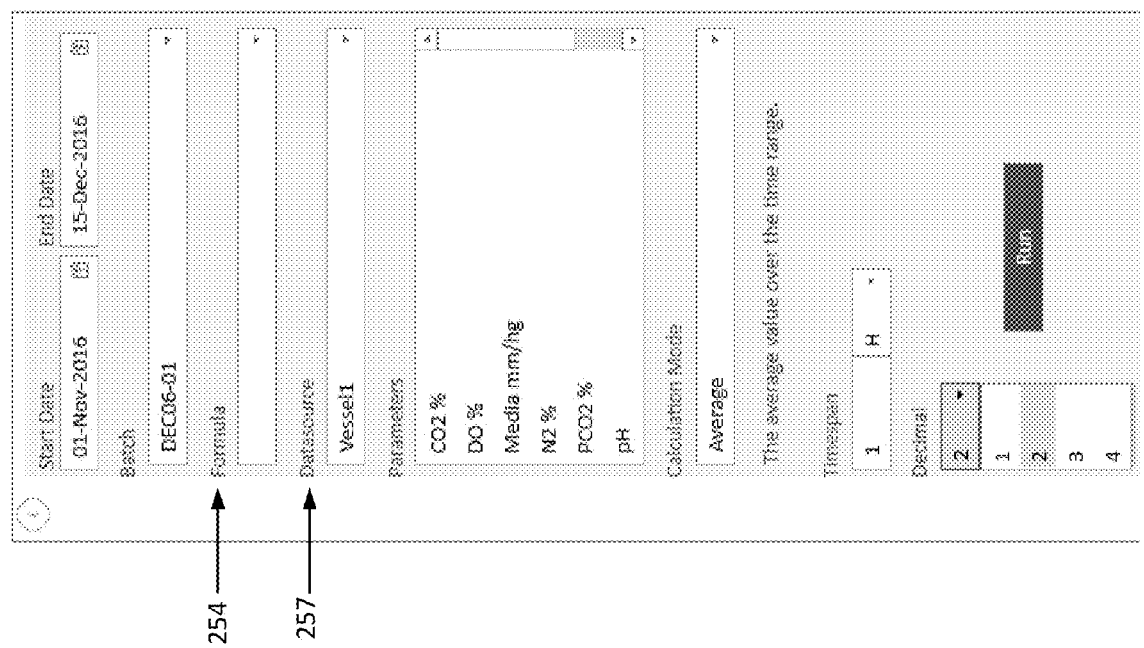
FIG. 30 shows an interface for creating and applying a new formula to collected data, in accordance with illustrative embodiments of the invention.

FIG. 30 shows an interface for creating and applying a new formula 254 to collected data. In a manner similar to FIG. 29, a batch is selected that will provide data for performing calculations. In illustrative embodiments the formula 254 may be created in the same interface shown, in a manner similar to FIG. 28. The user can select a data source 257, in this case, Vessel1.

FIG. 31 shows a formula spreadsheet 260 created by a formula. All of the data for the parameters used in the formula from the selected batch ID 190 are shown, along with the timestamp 234. The value of the formula (e.g., Vessel1Test) the user created/selected is also shown (e.g., the value under column N 262 for formula Vessel1Test). The formula values can be used to adjust active experiments (e.g., shown in live trends) or to adjust parameters for experiments that have yet to be run. For example, if glucose concentration is high, the bioprocess management unit 122 may monitor the concentration and adjust the set point to the pump accordingly. In addition, a predictive model/analytics based on historical data of a past run is built into the bioprocess management unit 122 to provide the user with a window on how well the batch is running to achieve the goal of each run.

Illustrative embodiments of the invention may have drivers configured to output collected data to a third-party analytics engines. Multivariable data analysis software requires data preparation, and the bioprocess management unit 122 may automatically format collected data and seamlessly output the data to the third-party analytics engine. One example of a third-party analytics engine is SIMCA. SIMCA is a third-party software that researchers use to study and evaluate multivariable processes. Among other things, SIMCA analyzes process variations, identifies critical parameters, and predicts final product quality. SIMCA requires input data from the process in order to produce the desired results.

The bioprocess management unit 122 may have a built-in software interface that will take the collected experimental data and set up the data according to SIMCA's data requirements. When the user collects a specific dataset from the process, they may enter a project name that they desire to create in SIMCA, then press a button to automatically set up the proper format and start SIMCA with the user's desired project name and dataset. This may save researchers the time it takes to prepare the data. Although SIMCA is used as an example, it should be understood that illustrative embodiments may operate as described above with other third-party analytics software (e.g., JMP).

Figure 32:
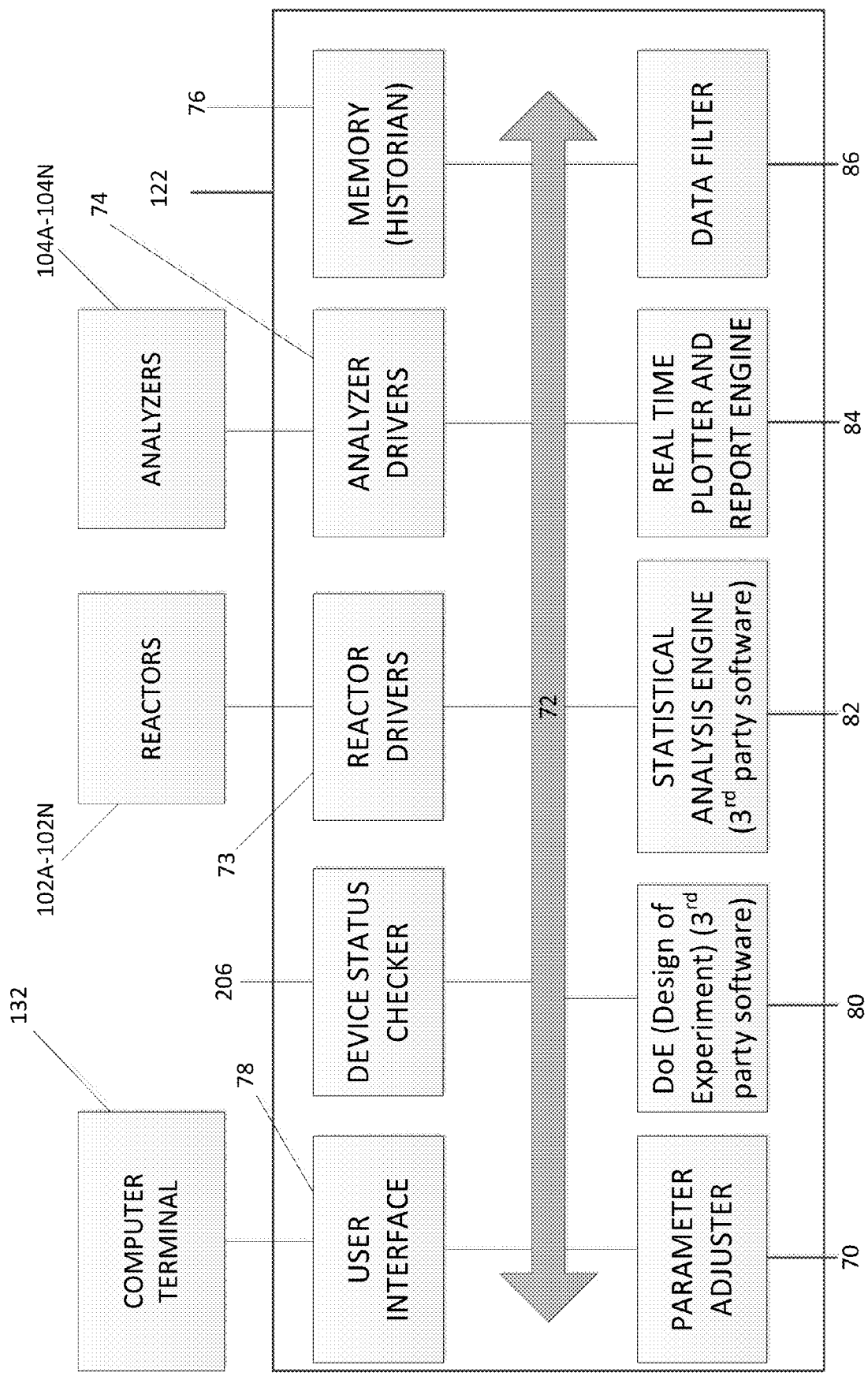
FIG. 32 schematically shows details of a bioprocess management unit in accordance with illustrative embodiments of the invention.

FIG. 32 schematically shows the plurality of data utilization functionalities enabled by the bioprocess management unit 122. As discussed above, the bioprocess management unit 122 enables communication of a variety of disparate bioreactors 102A-102N and analyzers 114A-114N. As an example, bioreactors 102A-102N may output continuous data every second for 17 days, and analyzers 104A-104N may output intermittent data (also referred to as "discrete" data) every 3-10 minutes for 17 days.

FIG. 32 schematically shows details of a bioprocess management unit 122 in accordance with illustrative embodiments of the invention. Each of these components is operatively connected by a conventional interconnect mechanism. FIG. 32 simply shows a bus 72 communicating with each of the components. Those skilled in the art should understand that this generalized representation can be modified to include other conventional direct or indirect connections. Accordingly, discussion of the bus 72 is not intended to limit various embodiments.

The components include a parameter adjuster 70 configured to adjust the bioreactor operating parameters. The adjustments may be made, for example, based on data received from the bioreactors and/or analyzers, golden batch, and/or rules set by the user. To that end, the bioprocess management unit 122 has bioreactor drivers 72 and analyzer drivers 74 configured to receive data from a plurality of different bioreactors 102A-102N and analyzers 104A-104N. The system also has a status checker 206 that indicates whether the devices on the network are connected. The status checker 206 pings all of the connected devices on the network, and displays whether devices are connected or not on a user interface 78.

The bioreactor drivers 72 are also configured to output instructions to the bioreactor. Furthermore, the bioprocess management unit 122 has a memory 76 that allows the data to be stored, including golden batch data. Additionally, the unit has the user interface 78 so that manual adjustments may be made (e.g., bioreactor operating parameters). For example, minimums and maximums for parameter values may be set, and the parameter adjuster 70 may adjust the parameters once they reach/pass the set limits.

The parameter adjuster 70 is coupled to a variety of components that provide data. The parameter adjuster 70 takes the data and outputs instructions to the bioreactors. For example, the bioprocess management unit 122 has drivers configured to receive data from third party design of experiment 80 software. The design of experiment 80 software allows hypothetical experiments to be run at test parameters, without having to run the actual experiment. For example, a test can be run to see what the impact of pH is on cell density, and model results are provided. Parameter data may be received from the design of experiment 80 software, and the design of experiment 80 parameters may be converted to bioreactor operating parameters and stored in memory 76. The data may then be accessed by the parameter adjuster 70 to set the bioreactor operating parameters to match the design of experiment 80 parameters.

The statistical analysis engine 82 provides statistical analysis on the data provided by the bioreactors 102A-102N and/or analyzers 104A-104N. As described previously, users can create formulas and use the calculated results to control the bioreactor operating parameters. The formulas may be run in real time. To that end, the unit 122 also has a real time plotter and report engine 84. The real time plotter and report engine 84 displays real-time data collected from connected devices, and allows the parameter adjuster 70 to adjust bioreactor operating parameters in real time.

The bioprocess management unit 122 also has a data filter 86 that filters the data received from the bioreactors 102A-102N and analyzers 104A-104N. Because large amounts of data are received, users may only wish to receive data pertaining to certain parameters. The data filter 86 allows the user to choose the parameters for which they wish to receive data.

It should be noted that FIG. 32 only schematically shows each of these components. Those skilled in the art should understand that each of these components can be implemented in a variety of conventional manners, such as by using hardware, software, or a combination of hardware and software, across one or more other functional components. For example, the parameter adjuster 70 may be implemented using a plurality of microprocessors executing firmware. As another example, the parameter adjuster 70 may be implemented using one or more application specific integrated circuits (i.e., "ASICs") and related software, or a combination of ASICs, discrete electronic components (e.g., transistors), and microprocessors. Accordingly, the representation of the parameter adjuster 70 and other components in a single box of FIG. 32 is for simplicity purposes only. In fact, in some embodiments, the parameter adjuster 70 of FIG. 32 is distributed across a plurality of different machines—not necessarily within the same device.

It should be reiterated that the representation of FIG. 32 is a significantly simplified representation of an actual bioprocess management unit 122. Those skilled in the art should understand that such a device has many other physical and functional components, such as central processing units, packet processing modules, and short-term memory. Accordingly, this discussion is in no way intended to suggest that FIG. 32 represents all of the elements of the bioprocess management unit 122.

Although the above discussion refers to bioreactors, it should be understood that illustrative embodiments may equally be applicable to other types of vessels/reactors. Thus, the bioprocess management unit 122 may be referred to more generally as a process management unit 122 when it is used non-exclusively with bioreactors. For example, illustrative embodiments of the invention may be used with chemical reactors.

Unless the context otherwise requires, chemical reactors may replace some or all of the bioreactors. Similar to bioreactors, chemical reactors comprise a vessel having operating parameters. Indeed, the chemical reactors may be of the same type as the bioreactor (e.g., continuous stirred-tank reactors, continuous flow stirred-tank reactors, etc., singularly or in series,). Instead of cell cultures and/or proteins, however, chemical reactors contain chemical reactions that produce a desired chemical product (e.g., chemical compound or molecule).

FIG. 33 is a flowchart 3300 schematically illustrating an experiment, in accordance with one exemplary embodiment of the invention. It should be noted that this method is substantially simplified from a longer process that may normally be used. Accordingly, the method of FIG. 33 may have many other steps that those skilled in the art likely would use. In addition, some of the steps may be performed in a different order than that shown, or at the same time. Those skilled in the art therefore can modify the process as appropriate.

The process begins at block 3302, where the experiment begins in the reactor. The experiment may grow cells and/or proteins in one or more bioreactors. Alternatively, the experiment may produce chemical compounds from a chemical reaction in one or more chemical reactors. Bioreactors and chemical reactors may generally be referred to as reactors. Before the experiment begins, the reactor operating parameters may be set. The technician may manually input the values for the operating parameters into the user interface of the reactor. Alternatively, the user may input the values for the operating parameters into the user interface of the process management unit.

Another option for setting the reactor operating parameters includes taking the values from a template having preconfigured values for all of the parameters, as described previously with reference to FIG. 25. For example, the experiment may wish to use template parameter values from a golden batch. Alternatively, the experiment may wish to use parameter values from a theoretical design of experiment. The process management unit may automatically map the template parameter values to the reactor operating parameters, and the experiment can be started. Template parameter values may also be adjusted as necessary through the process management unit.

After the parameter values have been established, the experiment can be started from the process management unit. The reactor collects data relating to the operating parameters in real-time. As shown in block 3304, at any time during the experiment, a sample may be drawn from the reactor and placed into one or more analyzers. The analyzer collects data relating to the sample, such as data about parameters that are generally not tested for by the reactor. Samples may also be frozen and stored for testing in the analyzer at a later time. As described in FIG. 22, the analyzer data may later be adjusted to have a timestamp of when the sample was drawn, rather than when it was tested.

The reactors and the analyzers are connected to the process management unit. As such, they relay real-time data to the process management unit. As shown in block 3306, the reactor data and analyzer data may be plotted in real-time. All, or a selection, of the collected parameters can be plotted simultaneously. Furthermore, previously run experiments (such as the golden batch), or simulated data experiments can also be plotted alongside the real time data. It should be noted that multiple reactors and multiple analyzers can be plotted simultaneously, regardless of brand of device and/or the geographic location of the device. Additionally, the actual data values can be seen in real time (e.g., in a table format).

The plots can be monitored in real time to see if any adjustments are necessary. As shown in block 3308, the bioreactor operating parameters can be modified in real-time. If adjustments need to be made, the adjustments to the parameter values can be made manually by a technician looking at the real-time data. Additionally, or alternatively, the adjustments to the parameter values can be made using the process management unit. The process management unit is able to separately or uniformly adjust reactor operating parameters for all connected reactors. The parameters can be automatically adjusted, repeatedly, based on, for example: a maximum and/or minimum limit for a certain reactor operating parameters, to mimic operating parameters from golden batches, data received from the analyzer, and/or based on a feedback loop from a formula created in the process management unit.

As adjustments are made to reactor operating parameters, the plots continue to be plotted in real time. The process management unit is able to continuously modify reactor operating parameters as necessary during the course of the experiment. Additionally, the process management unit can make these modifications individually or universally to any connected reactor. If no more adjustments need to be made to the experiment, then the process moves to step 3310, and the experiment is finished.

Although illustrative embodiments discuss an experimental process, it should be understood that this process is merely intended as an example. The same process may be used for other processes, such as a manufacturing process.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

What is claimed is:

1. A bioprocess management system comprising:
a bioprocess management controller configured to electronically interface one or more bioreactor and one or more analyzer,
  wherein each bioreactor is configured to maintain a population of cells based on a set of bioreactor operating parameters and to output bioreactor data,
  wherein each analyzer is configured to analyze at least one sample taken from at least one of the one or more bioreactor, each analyzer further configured to output analyzer data for each sample,
the bioprocess management controller configured to:
  receive the bioreactor data and the analyzer data in real-time,
  correlate, in real-time, the analyzer data from at least one of the one or more analyzer with the bioreactor data from the at least one of the one or more bioreactor from which the sample corresponding to the analyzer data was taken, and
  output real-time data based at least in part on the correlated data from the at least one of the one or more analyzer and the at least one of the one or more bioreactor.

2. The bioprocess management system as defined by claim 1, wherein the sample comprises at least a portion of the population of cells.

3. The bioprocess management system as defined by claim 2, wherein the bioprocess management controller is configured to adjust at least one bioreactor operating parameter to mitigate or prevent death of the cells in response to the real-time data.

4. The bioprocess management system as defined by claim 1, wherein the bioprocess management controller is configured to output the real-time data as graphical indicia.

5. The bioprocess management system as defined by claim 1, wherein the bioprocess management controller is configured to repeatedly adjust at least one bioreactor operating parameter based at least in part on the real-time data.

6. The bioprocess management system as defined by claim 5, wherein the bioprocess management controller is configured to perform a calculation on the real-time data according to a formula, the calculation being used to adjust the at least one bioreactor operating parameter.

7. The bioprocess management system as defined by claim 5, wherein the bioprocess management controller is configured to automatically adjust the at least one bioreactor operating parameter based on comparisons between the real-time data and batch data in memory,
the batch data in memory being golden batch data.

8. The bioprocess management system as defined by claim 1, further comprising the one or more bioreactor and the one or more analyzer.

9. The bioprocess management system as defined by claim 1, wherein at least one of the bioreactor operating parameters is imported from a template.

10. The bioprocess management system as defined by claim 1, wherein the bioprocess management controller is configured to synchronize the bioreactor data and the analyzer data and to display the synchronized data simultaneously in real-time.

11. The bioprocess management system as defined by claim 1, wherein the bioprocess management controller includes a driver for each bioreactor and a driver for each analyzer,
the bioprocess management controller receiving the bioreactor data and analyzer data using the drivers.

12. A method of managing bioreactor operating parameters comprising:
electronically interfacing a bioprocess management controller with one or more bioreactor and one or more analyzer,
wherein the each bioreactor is configured to maintain a population of cells based on a set of bioreactor operating parameters and to output bioreactor data,
wherein the each analyzer is configured to analyze at least one sample taken from at least one of the one or more bioreactor, each analyzer further configured to output analyzer data for each sample;
receiving, by the bioprocess management controller, the bioreactor data and the analyzer data in real-time;
correlating, by the bioprocess management controller in real-time, the analyzer data from at least one of the one or more analyzer with the bioreactor data from the at least one of the one or more bioreactor from which the sample corresponding to the analyzer data was taken; and
outputting, by the bioprocess management controller, real-time data based at least in part on the correlated data from the at least one of the one or more analyzer and the at least one of the one or more bioreactor.

13. The method as defined by claim 12, wherein the real-time data is output as graphical indicia.

14. The method as defined by claim 12, further comprising:
adjusting at least one bioreactor operating parameter based at least in part on the real-time data.

15. The method as defined by claim 14, further comprising:
performing a calculation on the real-time data with a formula, the calculation being used to adjust the at least one bioreactor operating parameter.

16. The method as defined by claim 12, wherein the at least one reactor operating parameter is adjusted based on comparisons between the real-time data and batch data in memory,
the batch data in memory being golden batch data.

17. The method as defined by claim 12, further comprising:
receiving the bioreactor and the analyzer data using a driver for electronically interfacing with the at least one bioreactor and the at least one analyzer.

18. The method as defined by claim 12, further comprising:
importing at least one initial bioreactor operating parameter from a template.

19. The method as defined by claim 12, wherein the sample comprises at least a portion of the population of cells.

20. The method as defined by claim 12, further comprising adjusting, by the bioprocess management controller, at least one bioreactor operating parameter to mitigate or prevent death of the cells in response to the real-time data.

* * * * *